(12) United States Patent
Trombley, III et al.

(10) Patent No.: US 7,540,854 B2
(45) Date of Patent: Jun. 2, 2009

(54) METHOD OF SUBSTITUTING A FIRST FLUID DELIVERY DEVICE WITH A SECOND FLUID DELIVERY DEVICE

(75) Inventors: Frederick W. Trombley, III, Gibsonia, PA (US); Francis J. Sciulli, Jr., Crafton, PA (US); David M. Griffiths, Pittsburgh, PA (US); Arthur E. Uber, III, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 700 days.

(21) Appl. No.: 10/190,361

(22) Filed: Jul. 3, 2002

(65) Prior Publication Data

US 2003/0014035 A1 Jan. 16, 2003

Related U.S. Application Data

(60) Provisional application No. 60/304,386, filed on Jul. 10, 2001.

(51) Int. Cl.
*A61M 37/00* (2006.01)
*A61B 6/00* (2006.01)

(52) U.S. Cl. .................. 604/131; 600/431

(58) Field of Classification Search .......... 604/506, 604/507, 508, 518, 80, 81, 82, 83, 86, 93.01, 604/131, 151, 153, 257, 258, 262, 284, 533
See application file for complete search history.

(56) References Cited

U.S. PATENT DOCUMENTS 3,966,358 A 6/1976 Heimes et al.

(Continued)

FOREIGN PATENT DOCUMENTS

DE 197 14 711 10/1998

(Continued)

OTHER PUBLICATIONS

Keeler, E. K. et al., Accessory Equipment Considerations With Respect to MRI Compatibility, *JMRI*, vol. 8, No. 1 (Jan./Feb. 1998).

(Continued)

*Primary Examiner*—Kevin C Sirmons
*Assistant Examiner*—Elizabeth R Moulton
(74) *Attorney, Agent, or Firm*—James R. Stevenson; Gregory L. Bradley; Henry E. Bartony, III

(57) ABSTRACT

A method of substituting an MRI incompatible pump for delivering fluid to a patient with an MRI compatible pump, both pumps being microprocessor controlled. The first pump operates upon administration tubing for pumping fluid from a source thereof to the patient. The method includes the steps of: providing the second pump to be substituted for the first pump; providing second tubing having a portion thereof that is operable to function with the second pump; connecting the second tubing to the administration tubing to establish an altered fluid path from the source to the patient, the altered path including portions of both the administration and second tubing; placing the second pump for operation upon the second tubing to enable the second pump to pump the fluid through the altered path according to programming thereof; and disconnecting the first pump from the administration tubing before bringing the patient into the MRI environment.

8 Claims, 19 Drawing Sheets

U.S. PATENT DOCUMENTS

| | | | |
|---|---|---|---|
| 4,255,088 A | 3/1981 | Newton et al. | |
| 4,277,226 A | 7/1981 | Archibald | |
| 4,396,385 A | 8/1983 | Kelly et al. | |
| 4,457,751 A | 7/1984 | Rodler | |
| 4,460,535 A | 7/1984 | Kitoh et al. | |
| 4,617,014 A | 10/1986 | Cannon et al. | |
| 4,690,673 A | 9/1987 | Bloomquist | |
| 4,781,548 A | 11/1988 | Alderson et al. | |
| 4,798,590 A * | 1/1989 | O'Leary et al. | 604/153 |
| 4,854,836 A | 8/1989 | Borsanyi | |
| 4,946,439 A * | 8/1990 | Eggers | 604/67 |
| 4,954,812 A | 9/1990 | Lebron | |
| 4,966,579 A | 10/1990 | Polaschegg | |
| 5,018,945 A | 5/1991 | D'Silva | |
| 5,057,076 A | 10/1991 | Polaschegg | |
| 5,059,173 A * | 10/1991 | Sacco | 604/80 |
| 5,176,631 A | 1/1993 | Koenig | |
| 5,224,937 A * | 7/1993 | van der Heiden et al. | 604/200 |
| 5,290,239 A * | 3/1994 | Classey et al. | 604/131 |
| 5,417,213 A | 5/1995 | Prince | |
| 5,429,602 A | 7/1995 | Hauser | |
| 5,439,451 A | 8/1995 | Collinson et al. | |
| 5,494,036 A | 2/1996 | Uber, III et al. | |
| 5,515,851 A * | 5/1996 | Goldstein | 600/431 |
| 5,616,124 A | 4/1997 | Hague et al. | |
| 5,739,508 A | 4/1998 | Uber, III | |
| 5,792,056 A * | 8/1998 | Prince | 600/420 |
| 5,807,322 A | 9/1998 | Lindsey et al. | |
| 5,827,223 A | 10/1998 | Butterfield | |
| 5,840,058 A * | 11/1998 | Ammann et al. | 604/30 |
| 5,853,397 A | 12/1998 | Shemesh et al. | |
| 5,968,014 A * | 10/1999 | Neftel et al. | 604/151 |
| 6,064,797 A | 5/2000 | Crittendon et al. | |
| 6,083,206 A | 7/2000 | Molko | |
| 6,106,249 A | 8/2000 | Barak | |
| 6,106,502 A | 8/2000 | Richmond | |
| 6,203,528 B1 | 3/2001 | Deckert et al. | |
| 6,213,738 B1 | 4/2001 | Danby et al. | |
| 6,224,578 B1 | 5/2001 | Davis et al. | |
| 6,248,093 B1 | 6/2001 | Moberg | |
| 6,261,262 B1 | 7/2001 | Briggs et al. | |
| 6,471,674 B1 * | 10/2002 | Emig et al. | 604/131 |
| 6,650,929 B1 * | 11/2003 | Nemoto et al. | 600/431 |
| 2002/0127114 A1 | 9/2002 | Barak | |
| 2002/0177821 A1 | 11/2002 | Barak | |
| 2006/0079758 A1 * | 4/2006 | Susi | 600/420 |

FOREIGN PATENT DOCUMENTS

| | | |
|---|---|---|
| JP | HEI 7-178169 | 7/1995 |
| WO | WO 03/006101 | 1/2003 |

OTHER PUBLICATIONS

Lemieux L. et al., "Recording of EEG During fMRI Experiments: Patient Safety," *MRM*, 38: 943-952 (1997).

Lemieux, L. et al., "Methodological Issues in EEG-Correlated Functional MRI Experiments," *IJBEM*, vol. 1, No. 1, pp. 87-95 (1999).

"A Primer on Medical Device Interactions With Magnetic Resonance Imaging Systems," U. S. Food and Drug Administration, Center for Devices and Radiological Health (Feb. 7, 1997).

International Search Report for Counterpart PCT Application PCT/US02/21482.

BodyGuard Operator's Manual, Version 06, Caesarea Medical Electronics Ltd., Israel (May 2001).

BodyGuard Ambulatory Infusion Pump Product Brochure, Caesarea Medical Electronics, Ltd., Israel (no date).

Israeli Patent Application Serial No. 142446 filed Apr. 4, 2001, "A Flow Set and a Method to Identify Said Flow Set by a Liquid Pump" Caesarea Medical Electronics, Ltd., Israel.

Israeli Patent Application Serial No. 141137 filed Jan. 28, 2001, "Liquid Pump," Caesarea Medical Electronics, Ltd., Israel.

BodySet, IV Administration Set with Anti-siphon Valve, Male Luer Lock, CE0483, Manufactured by Teva Medical Ltd., Israel for Caesarea Medical Electronics, LTD, Israel (May 2001).

* cited by examiner

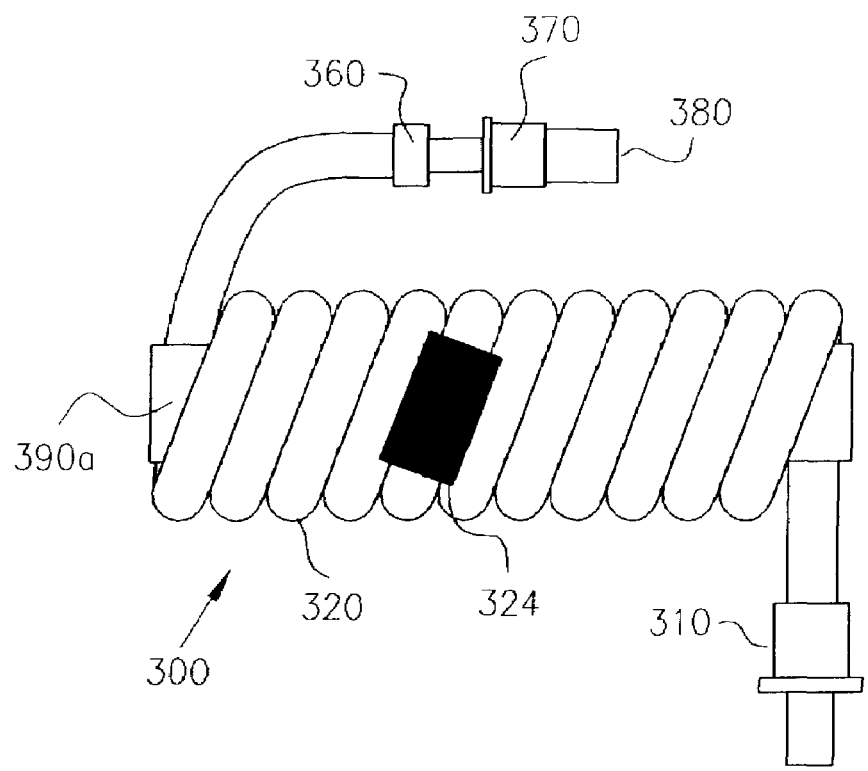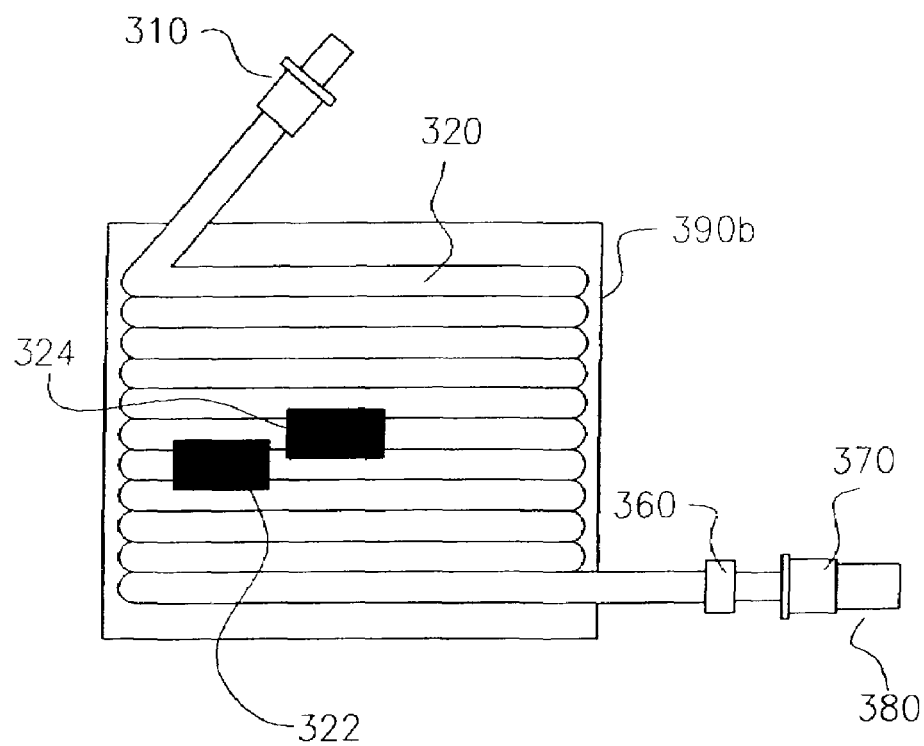
FIG. 4B

METHOD OF SUBSTITUTING A FIRST FLUID DELIVERY DEVICE WITH A SECOND FLUID DELIVERY DEVICE

CROSS REFERENCE TO RELATED APPLICATION

This application claims the benefit of U.S. Provisional Application Ser. No. 60/304,386, filed on Jul. 10, 2001, the contents of which are hereby incorporated by reference.

BACKGROUND OF THE INVENTION

The present invention relates to devices, systems and methods for infusion of fluid, and especially, to devices, systems and methods for use in the vicinity of a magnetic field of a magnetic resonance imaging system.

Magnetic resonance imaging (MRI) is used to image the body in a non-invasive manner. There are three types of electromagnetic fields used in MRI: a main static magnetic field (having field strengths from, for example, approximately 0.2 to several Tesla) which is generally homogeneous in the imaged volume; time varying magnetic gradient fields ($G_x$, $G_y$ and $G_z$), which have different orientations and operate at frequencies on the order of 1 kHz; and a radio frequency ("RF"; having, for example a frequency of approximately 63.87 MHz for a 1.5 Tesla static field strength).

MRI is often scheduled to image patients that may be attached to other types of equipment, such as ventilators, infusion pumps, or other devices. However, most of these devices fail to operate correctly in the high magnetic fields generated in MRI, create undesirable artifacts in the resultant image, and/or contain ferrous materials that are susceptible to magnetic fields. As a result, there are a substantial number of MRI procedures that are severely hampered, delayed or canceled because the patient cannot be connected to the needed equipment during the MRI procedure. A review of issues related to the compatibility of various equipment in an MRI environment is set forth in Keeler, E. K. et al., "Accessory Equipment Considerations with Respect to MRI Compatibility," *JMRI*, 8, 1 (1998), the disclosure of which is incorporated herein by reference. See also, Lemieux, L. et al., "Recording of EEG During MRI Experiments: Patient Safety," *MRM*, 38, 943 (1997); and "A Primer on Medical Device Interactions with Magnetic Resonance Imaging Systems," U.S Food and Drug Administration—Center for Devices and Radiological Health (Feb. 7, 1997), the disclosures of which are incorporated herein by reference.

For example, many patients in intensive care or similar units receive one or more drugs necessary to stabilize vital body systems/functions intravenously with use of an infusion pump. Often, such patients, cannot be disconnected from the drug source/infusion pump for even the relatively short period of time required to perform an MRI scan. If the infusion pump is incompatible with an MRI environment, the procedure must be delayed until the patient is sufficiently stable to be removed from the infusion pump, the procedure must be foregone, or a very long tubing set must be used that allows the infusion pump to be maintained a safe distance from the MRI magnet. Even in the case that a long tubing set can be used, problems persist including, but not limited to, tripping hazards created by the lengthy tubing set, an undeliverable or wasted volume of often expensive medication contained within the length tubing set, inaccuracy in the control of flow/volume and inaccessibility of infusion pump controls to operators.

In general, many devices, including but not limited to infusion pumps, that contain electric actuators such as DC brush motors, step motors, brushless DC motors or other wound coil motors and solenoids often fail in a strong magnetic field as a result of damage to internal permanent magnets. Moreover, currents induced within the field windings of such devices from electromagnetic fields can cause overheating and potential damage to the windings and any connected electronic circuitry. The MRI magnetic field can also interfere with the device created magnetic field and prevent accurate operation.

Furthermore, differences in magnetic permeability of materials within the actuator and eddy currents induced within actuator windings can affect the homogeneity or uniformity of the MRI magnetic field, generating image artifacts. Actuators that use mechanical commutation, such as DC brush motors, can also generate radio frequency energy during switching which can induce unwanted artifacts upon the acquired MRI images.

To prevent damage to sensitive equipment in MRI procedures, U.S. Pat. No. 4,954,812 discloses a magnetic field alarm indicator to detect when the ambient magnetic field reaches unacceptable levels for equipment operation. After an alarm indication, the equipment can be moved farther from the MRI magnet or disconnected from the patient. An alarm indication can be of limited effectiveness, however, if the equipment must be placed physically close to the patient, such as for fluid administration, or if the equipment must be closely connected to the patient. The use of a magnetic field alarm indicator as disclosed in U.S. Pat. No. 4,954,812 also does not address the problems of unwanted effects on magnetic field homogeneity and commutation or switching artifacts.

A number of medical devices have been designed to operate within the relatively high magnetic field environment used for MRI. For example, U.S. Pat. No. 5,494,036, discloses an injector system that provides for decreased interference between the magnetic field used for producing diagnostic images and the magnetic fields generated by the electric motors used for driving the pistons of the contrast media injectors. Japanese Patent Application HEI 7-178169 and German Patent Application DE 197 14 711 A1 disclose use of piezoelectric-based actuators such as ultrasonic motors in an MRI environment in an effort to reduce the adverse effects experienced with other actuators.

Because of certain modifications that may be necessary for devices designed to operate within an MRI environment (that is, within the general environment present in the vicinity of an MR scanner), such devices can be considerably more expensive than similar devices not designed to operate in an MRI environment. Moreover, the functionality and/or operation of devices designed to operate within an MR environment can be different from similar devices not designed to operate in an MR environment.

Given, for example, the criticality of continuous administration of vital system maintenance drugs to certain patients, it is very desirable to develop systems, methods and devices for facilitating use of devices designed to operate within an MRI environment.

SUMMARY OF THE INVENTION

In one aspect, the present invention provides a tubing set including a length of tubing having at least a section thereof that is fabricated to function with an infusion pump. The tubing set further preferably includes a first valve that is removably connected to the length of tubing on a first end thereof. The first valve is preferably in a closed state when disconnected from the length of tubing. The tubing set also preferably includes a second valve on a second end thereof. The second valve is preferably in a closed state until connected to another fluid path component. The tubing set is preferably suitable for use in an MR environment.

The first valve can, for example, include a housing and a closing member that is biased in a closed position when the first valve is removed from connection with the length of tubing. The closing member can extend outside of the housing when in a closed position for ease of aseptic cleaning.

The second valve can be biased in a closed position when the second valve is connected to the length of tubing and prior to connection of the second valve to another fluid path component. For example, the second valve can include a housing and a closing member that is biased in a closed position. The closing member of the second valve can extend outside of the housing when in a closed position.

In another aspect, the present invention provides a method of replacing at least a first infusion pump in connection with a patient with at least a second infusion pump including the steps: closing a length of patient tubing connected to a patient to prevent backflow of blood therethrough, the patient tubing being in fluid communication at a first end thereof with a length of administration tubing, the administration tubing being in operative connection with the first infusion pump and being in fluid connection with a source of fluid, the patient tubing being in fluid connection with a patient catheter at a second end thereof; disconnecting the patient tubing from the administration tubing; connecting an intermediate length of tubing to the administration tubing, the intermediate tubing including at least a section thereof that is fabricated to function with the second infusion pump; placing the second infusion pump in operative connection with the intermediate tubing; removing the first infusion pump from operative connection with the administration tubing; and connecting the intermediate tubing to the patient tubing. As clear to one skilled in the art, the order of certain of the steps set forth in the above method (and other methods set forth below) may not be important to the overall operability or effectiveness of the method.

The method can further include the step of priming the intermediate tubing with fluid after connection thereof with the administration tubing. The intermediate tubing can, for example, be primed using the first infusion pump. The intermediate tubing can also be primed using the second infusion pump.

In one embodiment, the second infusion pump is more suitable for use in an MR environment than the first infusion pump.

The intermediate tubing can be connected to the patient tubing via a valve that is removably connected to the intermediate tubing. This valve can be in a closed state when disconnected from the intermediate tubing as described above. The method can further include the step of disconnecting the patient tubing from the intermediate tubing while leaving the valve connected to the first length of tubing. The method can also further include the steps of: disconnecting the administration tubing from the intermediate tubing; connecting the patient tubing to the administration tubing via the valve; and placing the first infusion pump in operative connection with the administration tubing. The valve can be disinfected prior to connecting the valve to the administration tubing. As described above, the valve can include a housing and a closing member that is biased in a closed position when the valve is removed from connection with the intermediate tubing. Once again, the closing member can extend outside of the housing when in a closed position to facilitate disinfecting or aseptic cleaning.

In the method, a first plurality of infusion pumps can be replaced by a second plurality of infusion pumps. For example, the second plurality of infusion pumps can be more suitable for use in an MR environment than the first plurality of infusion pumps. Likewise, a first multi-channel infusion pumps can be replaced by a plurality of infusion pumps. Moreover, a first plurality of infusion pumps can be replaced by second, multi-channel infusion pump.

In another aspect, the present invention also provides a method of replacing at least a first infusion pump in connection with a patient with at least a second infusion pump. The first infusion pump is in fluid connection with a length of patient tubing connected to a patient at one end and removably connected to a length of administration tubing at another end. The administration tubing is in fluid connection with a source of fluid and in operative connection with the first infusion pump. The method includes the steps: disconnecting the patient tubing from the administration tubing; connecting a length of intermediate tubing between the patient tubing and the administration tubing, the intermediate tubing including at least a section thereof that is fabricated to function with the second infusion pump; placing the second infusion pump in operative connection with the intermediate tubing; and removing the first infusion pump from operative connection with the administration tubing.

In a further aspect, the present invention provides a method of substituting at least a first infusion pump in connection with a patient with at least a second infusion pump for a period of time. As described above, the first infusion pump is in fluid connection with a length of patient tubing connected to a patient at one end and removably connected to a length of administration tubing at another end. The administration tubing is in fluid connection with a first source of injection fluid and in operative connection with the first infusion pump. The method includes the steps of: disconnecting the patient tubing from the administration tubing; connecting a length of intermediate tubing to the patient tubing, the intermediate tubing including at least a section thereof that is fabricated to function with the second infusion pump, the intermediate tubing further including a first valve removably connected on a first end thereof, the first valve being closed when disconnected from the intermediate tubing; connecting the intermediate tubing to the first source of injection fluid or to a second source of injection fluid; placing the second infusion pump in operative connection with the intermediate tubing for the period of time; and after the period of time, disconnecting the patient tubing from the intermediate tubing while leaving the first valve connected to the first length of tubing.

In another aspect, the present invention provides a method of substituting at least a first infusion pump in connection with a patient with at least a second infusion pump. The first infusion pump is in operative connection with a length of administration tubing, which is in fluid connection with a source of injection fluid and with the patient. The administration tubing includes at least one port. The method includes the steps of: connecting a length of a second tubing to the port of the administration tubing; the second tubing including at least a portion thereof that is fabricated to function with the second infusion pump; connecting the second tubing to the source of injection fluid; placing the second infusion pump in operative connection with the second tubing; and removing the first infusion pump from operative connection with the administration tubing. For example, the port of the administration tubing can be part of a Y-connector, T-connector, manifold or other similar fluid path element.

In still a further aspect, the present invention provides a replacement infusion pump system including: an infusion pump and a tubing set having a length of tubing. The length of tubing includes at least a section thereof that is fabricated to function with the infusion pump. The infusion pump and the tubing set are suitable for use in an MR environment. In one embodiment, the tubing set further includes a first valve removably connected on a first end of the length of tubing. The first valve is in a closed state when disconnected from the length of tubing as described above. The tubing can further include a second valve connected on a second end of the length of tubing. The second valve can be in a closed state when connected to the length of tubing until connected to another fluid path element. The system can further include an adapter to place an administration tubing set of another infusion pump in a free flow state after the other infusion pump has been removed from operative connection with the administration tubing set. The length of tubing can include at least one Y-connector to provide a connection port thereon in addition to the tubing ends.

The present invention provides for simple and efficient replacement or substitution of at least one infusion pump with at least one other infusion pump (for example, having different utility than the first infusion pump). Air is readily removed from the fluid path before infusion into the patient. Moreover, the tubing set(s) provided with or used with the first infusion pump is/are typically maintained in the fluid path system, facilitating airless reconnection of the first infusion pump and reducing complexity and cost. Furthermore, sterility is maintained throughout the process of substituting one pump for another and waste of injection fluid is minimized.

BRIEF DESCRIPTION OF THE DRAWINGS

FIG. 4B illustrates two embodiments of packaging components for efficient packaging and connection of the tubing sets of the present invention.

DETAILED DESCRIPTION OF THE INVENTION

In one aspect, the present invention provides a system and method for replacing a fluid pump (for example, an infusion pump) that is not designed for use in a particular environment or in a particular manner with a fluid pump that is designed for or better equipped for that environment or that manner of use. For example, an infusion pump not well suited for ambulatory use can be replaced by an infusion pump better suited for ambulatory use. In one embodiment, the present invention provides a system and method of replacing an infusion pump not designed for or not well suited for use in an MR environment with an infusion pump that is better designed for or more suitable for use in an MR environment (referred to hereinafter generally as an MR infusion pump). Infusion pumps and other fluid pumps indicated to be suitable for use in an MR environment include the Volumed μVP5000 available from Arcomed AG of Regensdorf, Switzerland, an infusion pump available from Ulrich GmbH & Co. KG of Ulm, Germany, the TomoJet MR available from Bruker AG of Fallanden, Switzerland and the BodyGuard Ambulatory Infusion Pump available from Caesarea Medical Electronics, Ltd. Of Caesarea, Israel. Allowing use of an MR infusion pump in an MR environment reduces the length of tubing required and places the infusion pump near to the operating personnel to facilitate control thereof.

As used herein, the term "infusion" refers to the generally continuous, slow introduction of fluid into the body, and especially into a vein. As used herein, the term "infusion pump" refers to low infusion rate pressurizing devices used in administering or infusing medical fluids. One skilled in the art will recognize that the benefits and advantages of the systems and method described herein also apply to other non-infusion types of fluid delivery.

Figure 1:
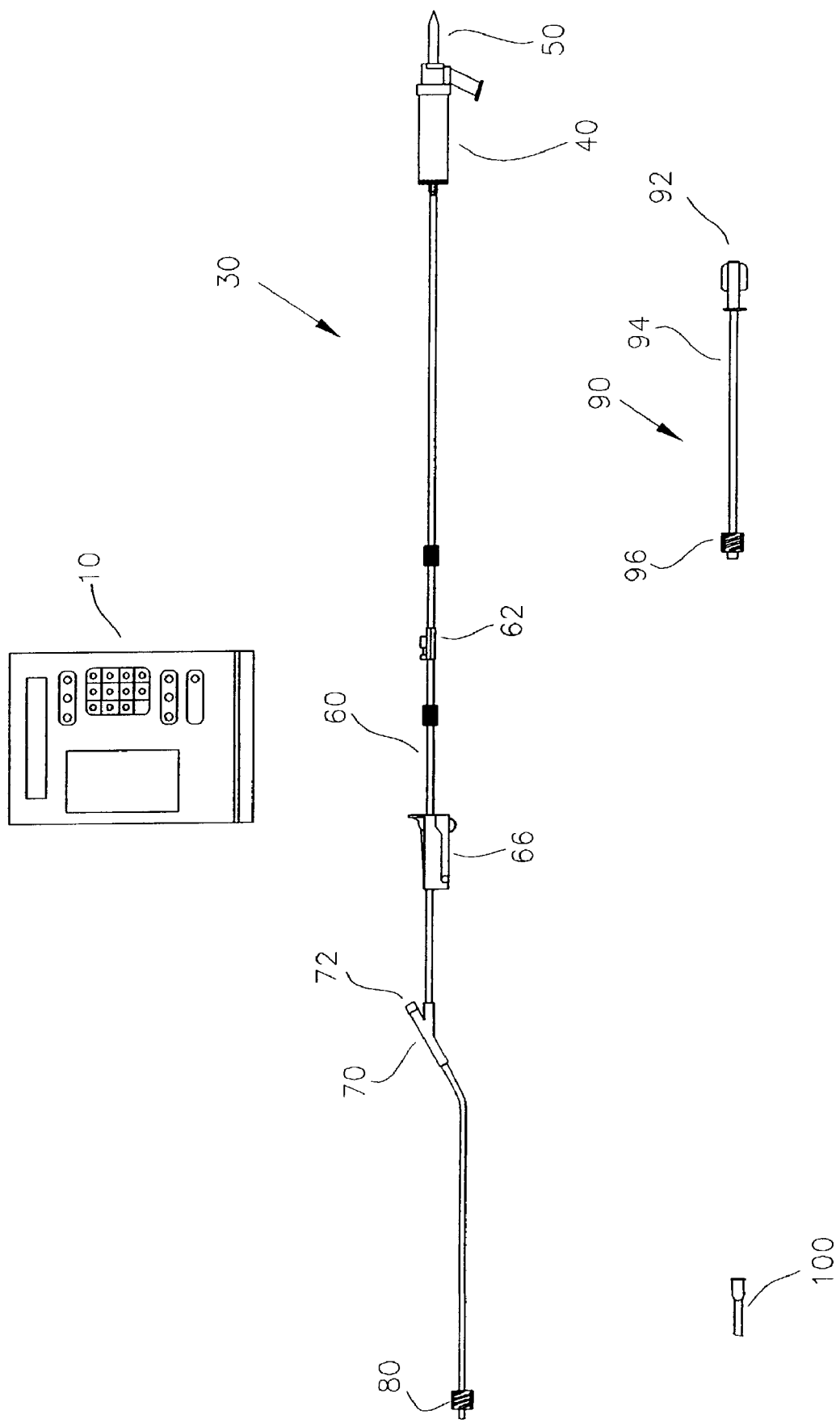
FIG. 1 illustrates a currently available infusion pump system in a disconnected state.
Figure 2:
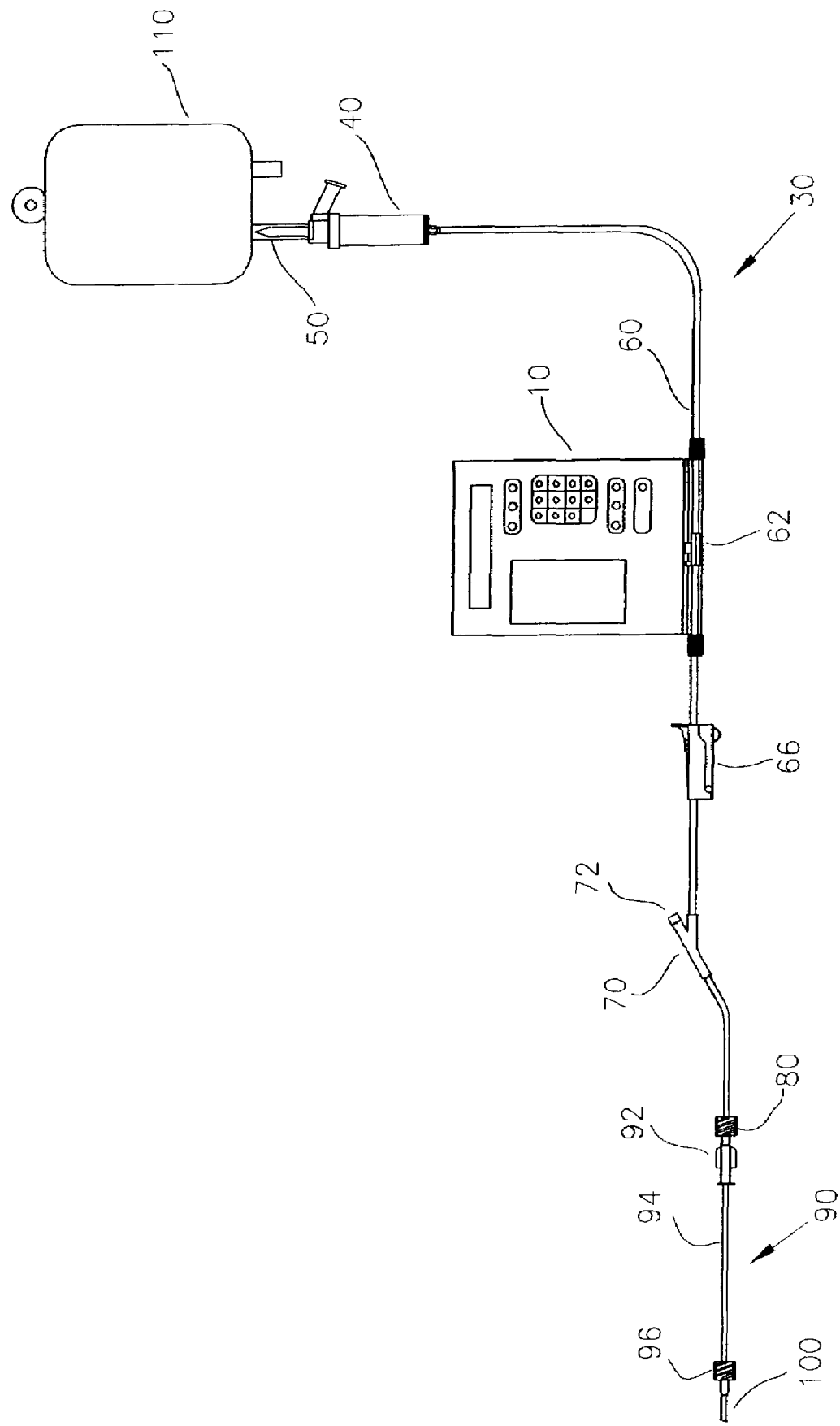
FIG. 2 illustrates the infusion pump system of FIG. 1 in a connected state and in fluid connection with a source of injection fluid.

FIGS. 1 through 14 illustrate one embodiment of a system and method as described above. In FIG. 1, a Colleague™ infusion pump 10 and associated administration tubing set 30 available from Baxter Healthcare Corporation of Deerfield, Ill. is illustrated. Tubing set 30 includes a barrett tube 40 having a spike 50 for forming a fluid connection with, for example, a standard IV bag 110 (see FIG. 2). The end of barrett tube 40 opposite spike 50 is in fluid connection with tubing 60 that is designed, fabricated or calibrated specifically (for example, having a specific inner diameter, outer diameter, durometer etc.) for use with infusion pump 10 as known in the art. Tubing 60 includes a pump key 62 that is required to operate with infusion pump 10. A roll clamp 66 is provided to stop flow through tubing set 60 if desired. Tubing set 30 also includes a Y-connector 70 including a port 72 for connecting another fluid source, manual syringe etc. to tubing set 60 as known in the art. Tubing set 30 terminates with a male luer connector 80. An extension set or patient tubing set 90 for tubing set 30 can also be provided. Extension set 90 includes a female luer connector 92 (to form a fluid connection with male luer connector 80) in fluid connection with a length of tubing 94. Tubing 94 terminates with a male luer connector 96. An IV catheter 100 can be attached to male luer connector 96. FIG. 2 illustrates infusion pump 10, tubing set 30, extension set 90 and catheter 100 in operative connection with IV bag, bottle or other injection fluid container 110.

Figure 3A:
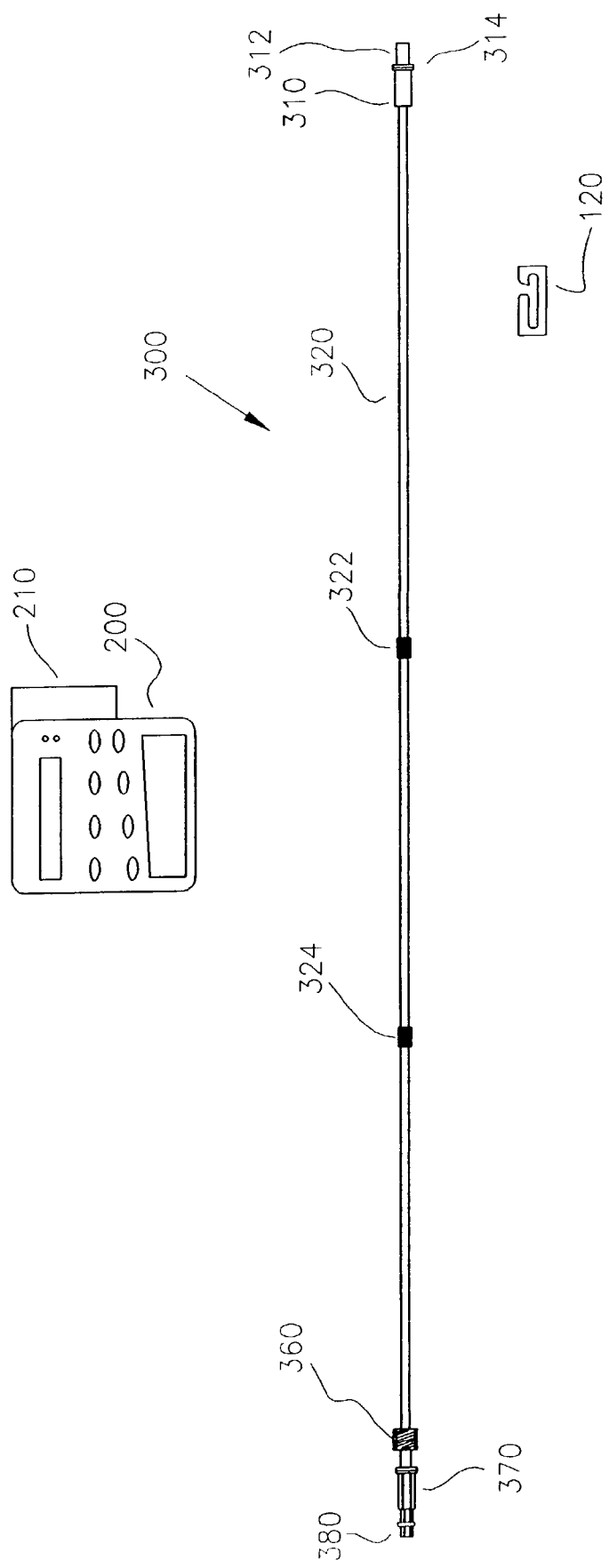
FIG. 3A illustrates an embodiment of a replacement infusion pump system of the present invention including an infusion pump and a tubing set for use with the infusion pump.

FIG. 3A illustrates an MR infusion pump 200 (for example, the BodyGuard Ambulatory Infusion Pump described above) and an associated fluid path or tubing set 300 that can be used to continue patient infusion in an MR environment. Tubing set 300 includes, on one end thereof, a fluid path component for stopping flow (when flow is not desired) such as an aseptic reflex valve 310 (for example, the Burron Aseptic Luer No. S5403000 available from the Burron OEM Division of B. Braun Medical of Bethlehem, Pa.). Other flow stop components suitable for use in the present invention include a clamp (for example, a roll clamp or a pinch clamp), a stopcock, a valve or a septum. Aseptic reflex valve 310 is described, for example, in U.S. Pat. No. 5,439,451, the disclosure of which is incorporated herein by reference. In general, aseptic cleaning of connector or valve 310 is facilitated by the position of the top surface of valve member 312 relative to outlet surface 314. In that regard, the top surface of a sealing member such as pin valve member 312 is biased outward to be preferably flush with or to extend outwardly from surface 314. A material carrying a disinfectant (for example, a cotton ball) can easily clean the entire surface of pin valve member 312. Moreover, valve member 314 is normally in a closed/sealed state (valve member 312 is biased outward until contacted by a male luer member), the interior of valve 310 is substantially protected from contamination from any source in the surrounding environment (whether airborne or via fluid or other contact).

Valve 310 is attached to tubing 320 having at least a portion thereof (for example, between markers 322 and 324) fabricated or designed (for example, having an appropriate inner diameter, outer diameter, durometer etc.) as known in the art for use with MR infusion pump 200. At the end of tubing 320 opposite valve 310, a male luer connector 360 is attached to tubing 320. Male luer connector 360 is preferably removably attached to a flow stop component (for example, a second aseptic reflex valve 370). A cap 380 can be used to prevent contamination of aseptic reflex valve 370.

Figure 3B:
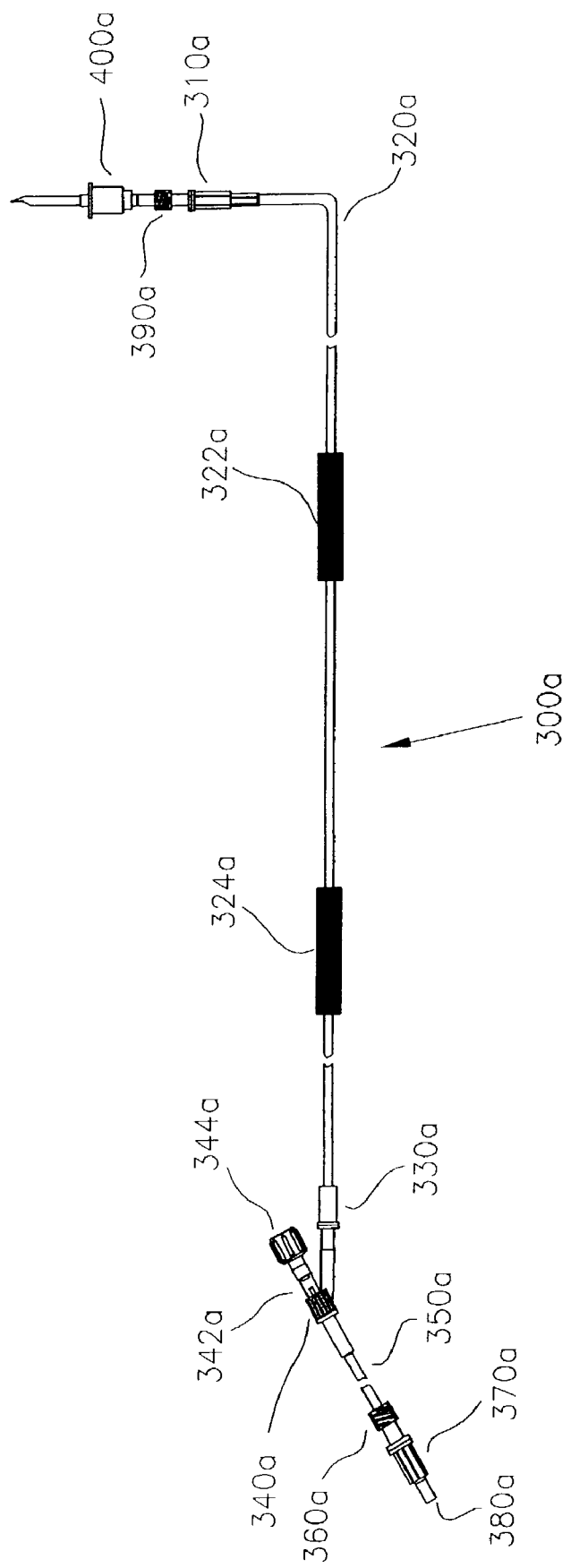
FIG. 3B illustrates another embodiment of a tubing set for use with the infusion pumps of the present invention.

FIG. 3B illustrates an alternative embodiment of a tubing set for use in the present invention. Tubing set 300a of FIG. 3B includes an aseptic reflex valve 310a as described above. Attached to valve 310a is a length of tubing 320a. As described above, at least a portion of tubing 320a (for example, between markers 322a and 324a, is designed as known in the art for use with MR infusion pump 200. Unlike tubing set 300, tubing set 300a includes a Y-connector 340a including, for example, a reflex valve connector 342a to which, for example, another fluid source (such as manual syringe or another infusion pump/fluid source combination) can be connected. The port of Y-connector 340a including reflex valve connector 342a is preferably in a normally closed position (that is, the port is closed until coupled with a male luer connector) to prevent backflow. A protective cap 344a can be used to protect a female luer fitting of reflex valve connector 342a and the associated port of Y-connector 340a from contamination. Y-connector 340 can, for example be connected to tubing 320a via a one-way check valve 330a such as the Burron Check Valve No. S5402010. Y-connector 340a is also attached to a second length of tubing 350a. A male luer connector 360a is connected to the end of tubing 350a opposite the end attached to Y-connector 340a. Male luer connector 350 is preferably attached to a second aseptic reflex valve 370a. A cap 380a can be used to prevent contamination of aseptic reflex valve 370a. Tubing set 300a can, for example, be attached to a bag spike 400a via a standard luer connector 390a.

Tubing set 300 and/or 300a can include encoding (for example, electrical, mechanical and/or optical encoding) to communicate information to, for example, infusion pump 200. Such information can, for example, include priming volume, tubing length, pressure rating, flow rate rating, durometer etc. Encoding of fluid path elements is described in U.S. Pat. No. 5,739,508, the disclosure of which is incorporated herein by reference. Infusion pump 200 can, for example, be provided with sensors such as optical or other sensors that are in communication with a microprocessor in infusion pump 200. A verification program can, for example, be provided to prevent use of tubing sets that are not properly encoded (and thus possibly not suited for use with MR infusion pump 200) from being used with MR infusion pump 200.

Tubing sets of the present invention such as tubing sets 300 and 300a are preferably suited for use in an MR environment in that (i) no component of the tubing set is substantially adversely affected by the magnetic fields of the MR imaging equipment (for example, subject to excessive force or subject to excessive induced currents) and (ii) no component of the tubing set substantially adversely affects the MR image (for example, by creating excessive artifacts). For example, the materials used in the tubing sets of the present invention preferably have low magnetic susceptibility and do not undergo large attraction forces or affect magnetic field homogeneity. For example, biasing members used in connectors 310, 310a, 370 and 370a can be polymeric. However, use of small amount of metallic material such as spring biasing member in components such as connectors 310, 310a, 370 and 370a has been found to not substantially adversely effect either the operation of the connector or the MR imaging equipment.

The tubing sets of the present invention can also be fabricated to be nonfunctional after a single use using methods known in the art. It may be desirable to prevent reuse to, for example, reduce the risk of cross-contamination between patients. Reuse of a particular encoded tubing set with one MR infusion pump can, for example, be prevented in the programming of the infusion pump.

Figure 4A:
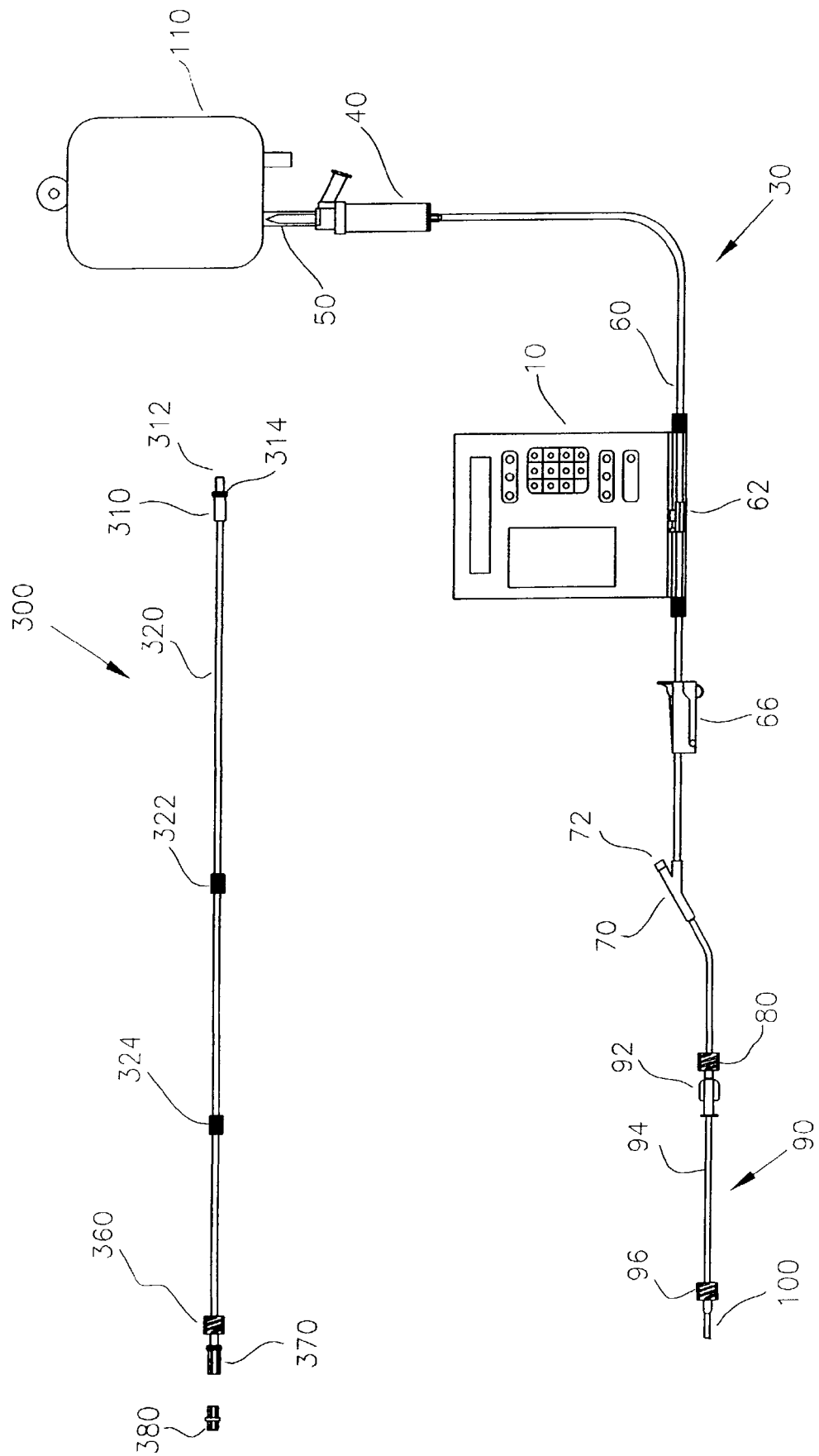
FIG. 4A illustrates removal of the tubing set of the present invention from its packaging and removal of an end cap therefrom in preparation for connection to the fluid path of FIG. 2.

FIG. 4A illustrates an initial step in one method of incorporating tubing set 300 or 300a of the present invention into a fluid delivery system originally including infusion pump 10, tubing set 30 and extension set 90. In that regard, tubing set 300 (or 300a) is preferably first removed from its packaging and cap 380 removed from valve 370. Preferably, tubing set 370 is packaged in a sterile condition as known in the art.

In several embodiments, tubing set 300 (or tubing set 300a) is packaged in a compacted or volume-reduced form to facilitate packaging and incorporation of tubing set 300 into, for example, the fluid delivery system of FIG. 2. For example, tubing set 300 can be wound around a cylindrical packaging element 390a. During the initial steps of incorporation/connection of tubing set 300a, only the length required for connection need be removed from around packaging element 390a, thereby preventing problems such as tangling and/or tripping that can occur upon complete unwinding. Tubing set 300 can be quite long (for example, 8 to 10 feet) in some embodiments, depending upon the distance from the MR equipment at which infusion pump 200 is preferably operated. In that regard, the degree to which MR infusion pumps suitably or desirably operate within the MR environment can vary between pumps and it may be desirable to maintain some distance between the MR infusion pump and the MR equipment to prevent failure of the MR infusion pump, undesirably large forces on the pump or image artifacts. FIG. 4B illustrates another packaging element 390b in which tubing 320 is packaged in a manner similar to Christmas tree lighting.

Figure 5:
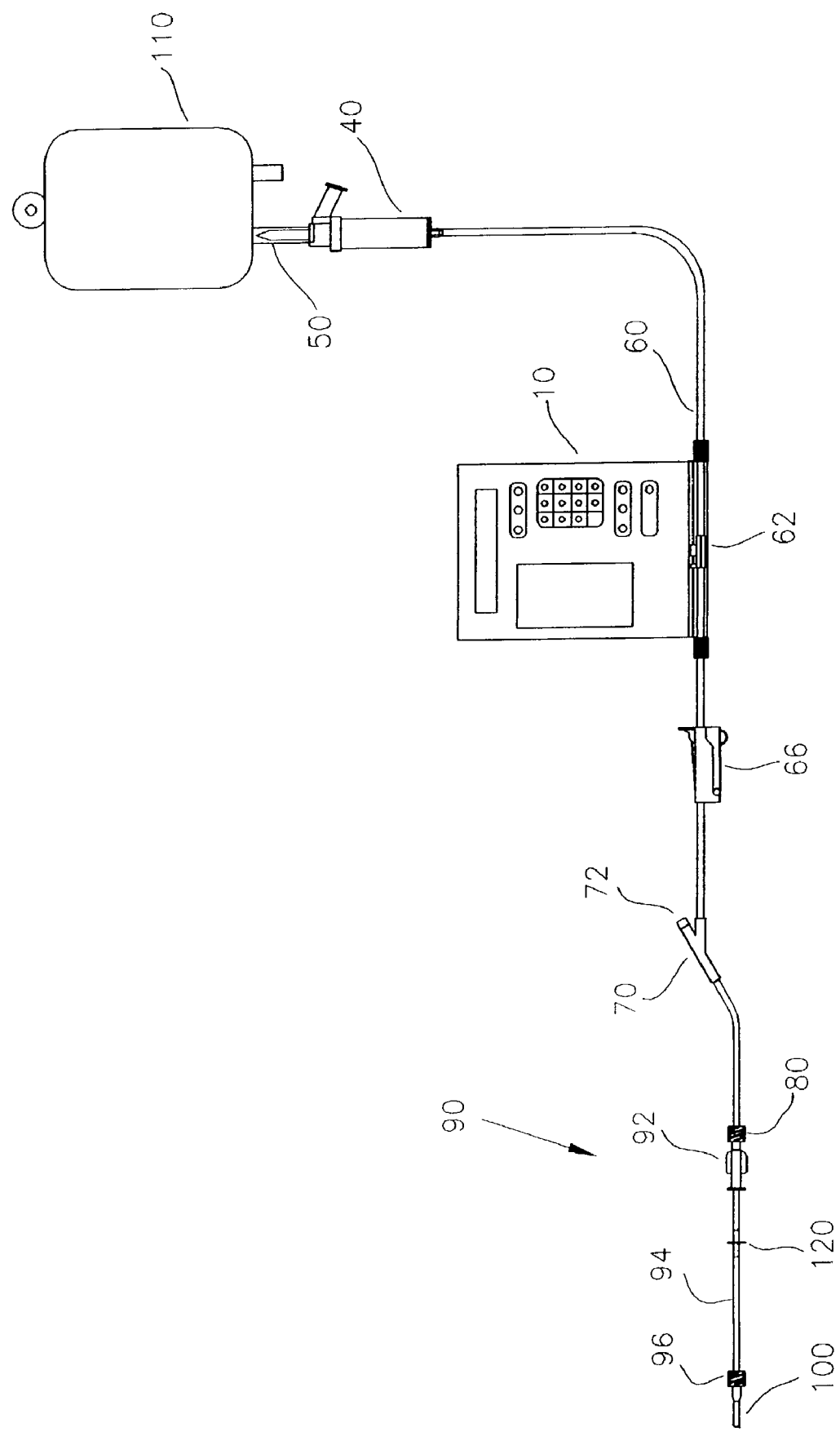
FIG. 5 illustrates the closing of the patient tubing of the fluid path of FIG. 2 to prevent backflow therethrough.
Figure 6:
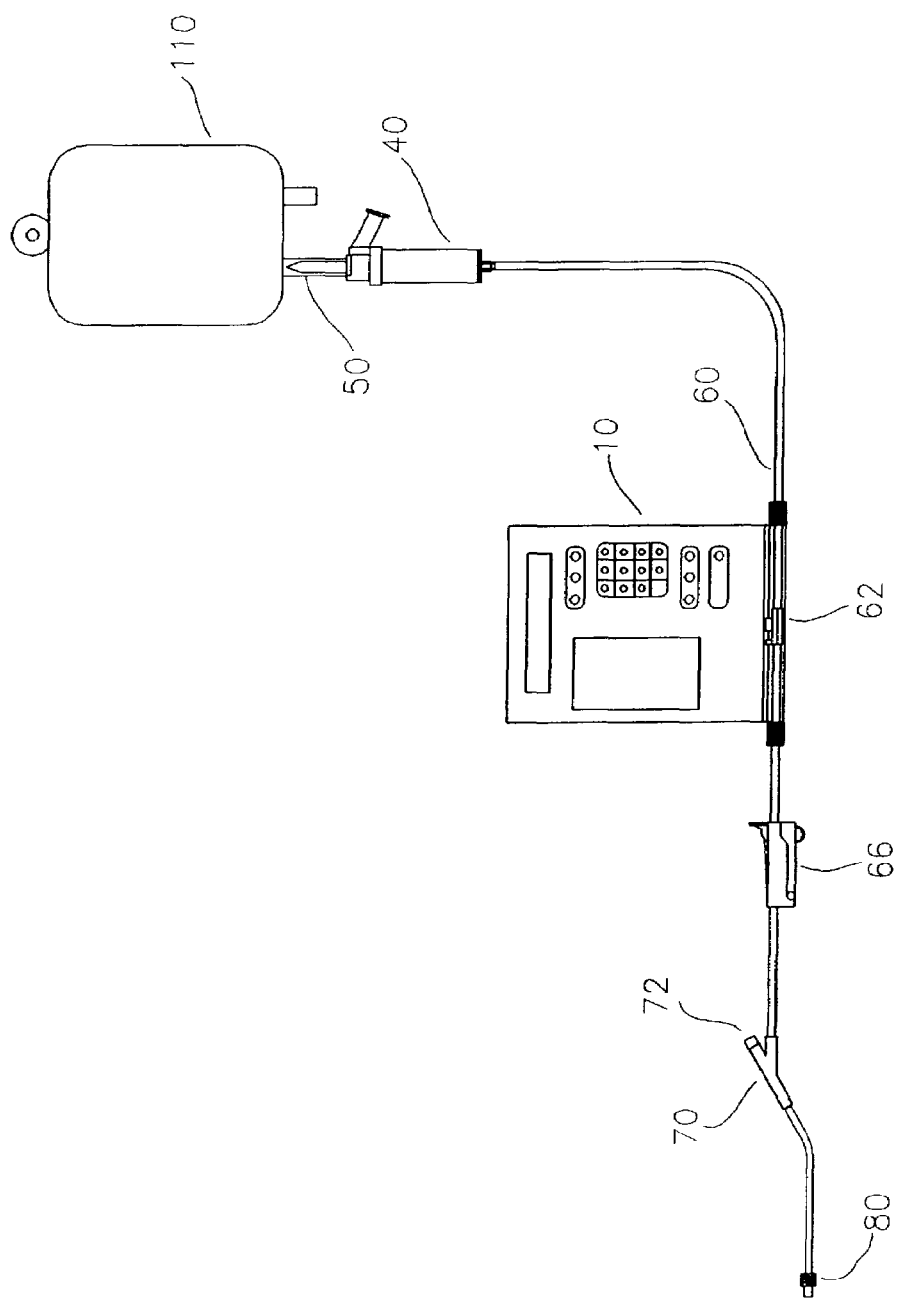
FIG. 6 illustrates detachment of the patient tubing from the administration tubing in preparation for incorporation of the tubing set of the present invention.
Figure 7:
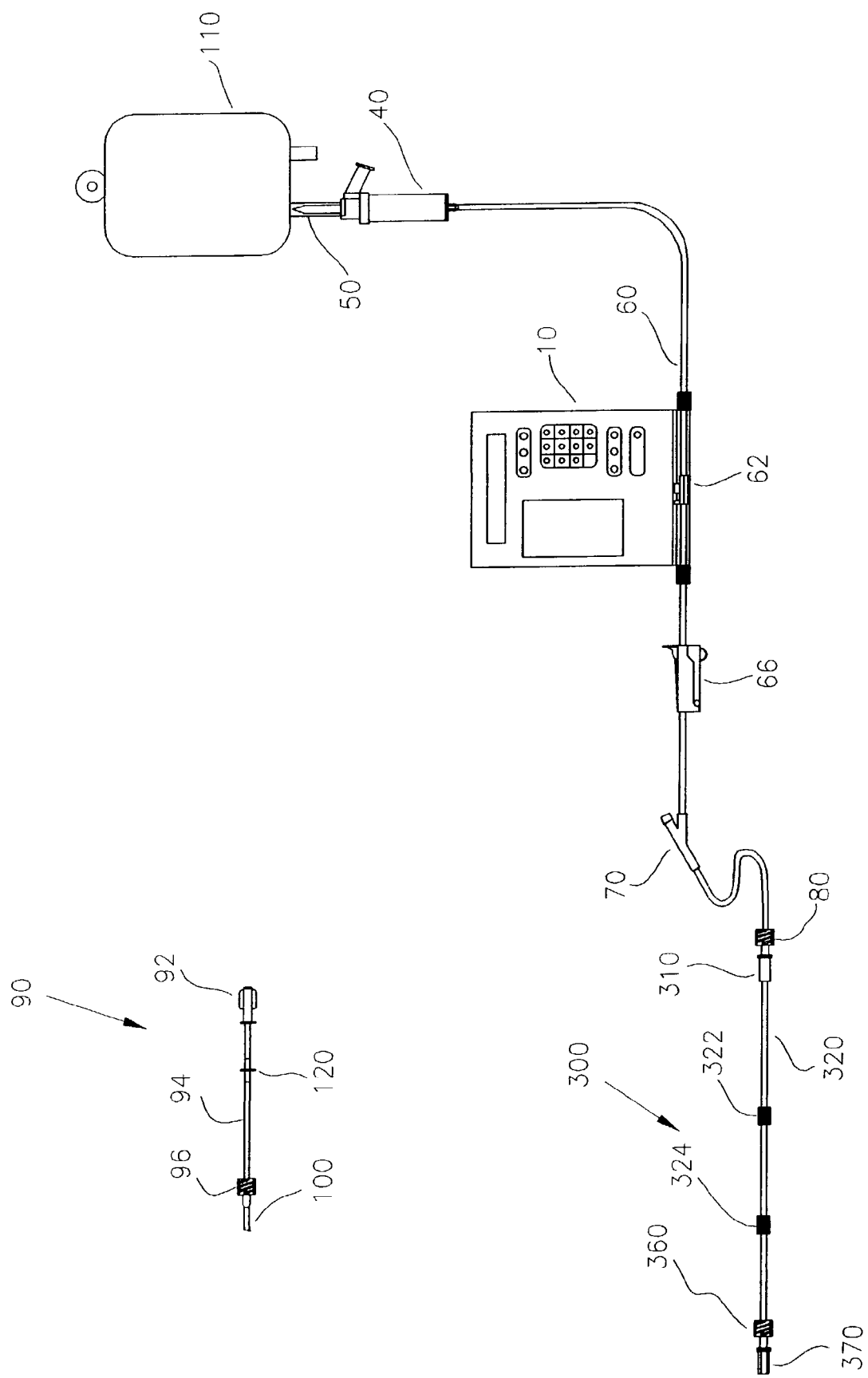
FIG. 7 illustrates attachment of the tubing set of the present invention to the administration tubing of FIG. 2.

As illustrated in FIG. 5, blood backflow from extension set 90 is preferably prevented (upon disconnection of extension set 90 from tubing set 30) by, for example, placing a clamp (for example, a slide clamp 120 as illustrated in FIG. 3A) on extension set 90. Clamp 120 can, for example, be shipped with tubing set 300. In one embodiment, cap 380 and clamp 120 were formed integrally. As illustrated in FIG. 6, after clamping extension set 90 (that is, preventing backflow therefrom), extension set 90 is disconnected form tubing set 30. After disconnection of extension set 90, tubing set 300 is attached to tubing set 30 via connection of valve 310 and male luer connector 80 as illustrated in FIG. 7. At this time, infusion pump 10 can be used to prime the fluid path as known in the art (that is, to displace gas or other fluid within the fluid path with the injection fluid), including tubing set 300, by forcing fluid from IV bag 110.

If tubing 60 does not allow flow therethrough (for example, free flow via gravity) without infusion pump 10 being in operative connection with tubing 60, it may be necessary to, for example, remove tubing set 30 and respike IV bag 110 with a spike connected to tubing set 300 or 300a or to provide another source of fluid. However, the system of the present invention can also include a flow element such as free flow element or adapter 210 shown attached to infusion pump 200 in FIG. 3A which is attachable to tubing 60, in a similar fashion, to pump 10, to cause free flow therethrough. In that regard, free flow element 210 preferably includes a mechanism or key operable in the same or similar manner as the mechanism of pump 10, which allows free flow through tubing 60.

Figure 8:
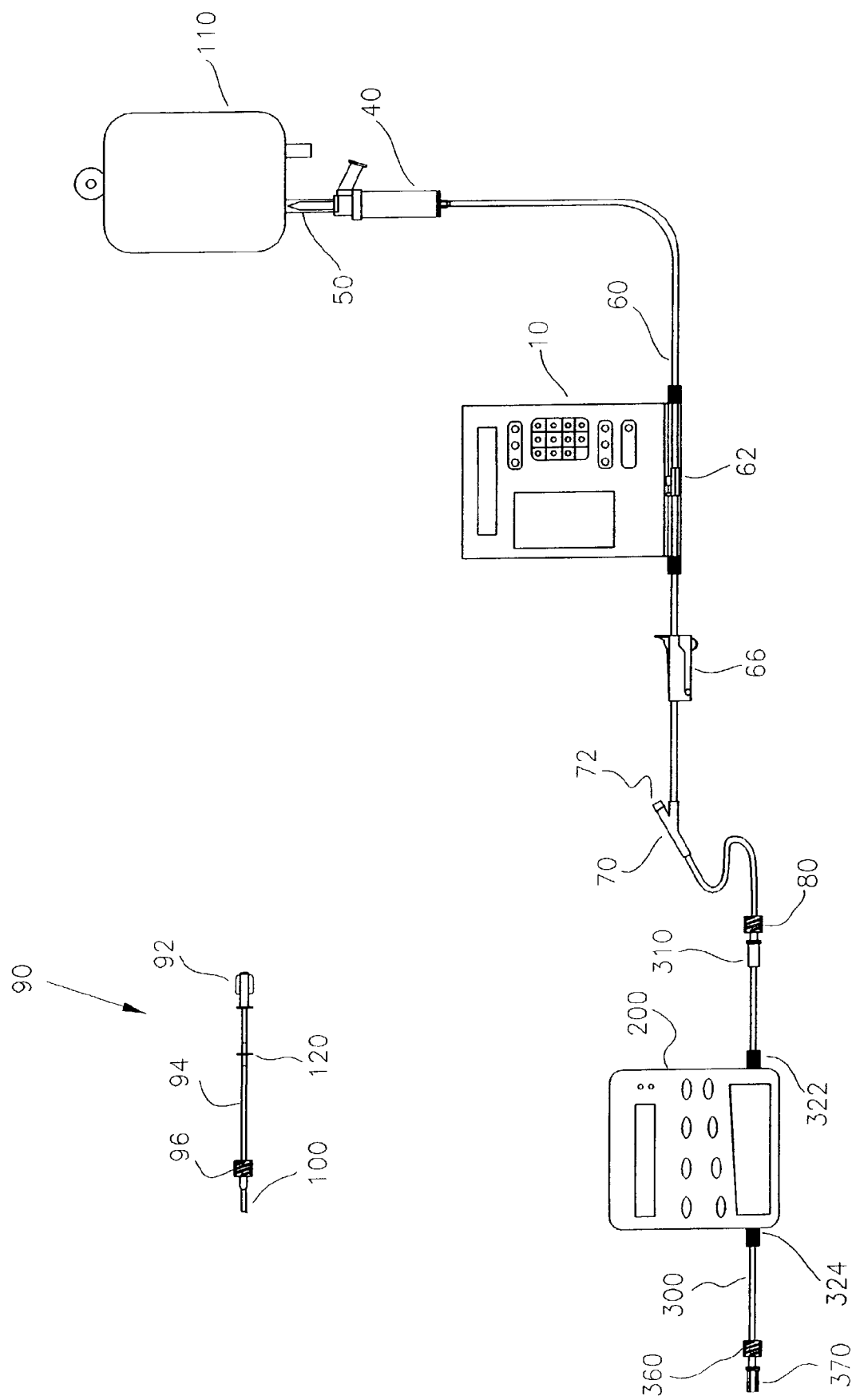
FIG. 8 illustrates connection of the replacement infusion pump to the tubing set of the present invention.
Figure 9:
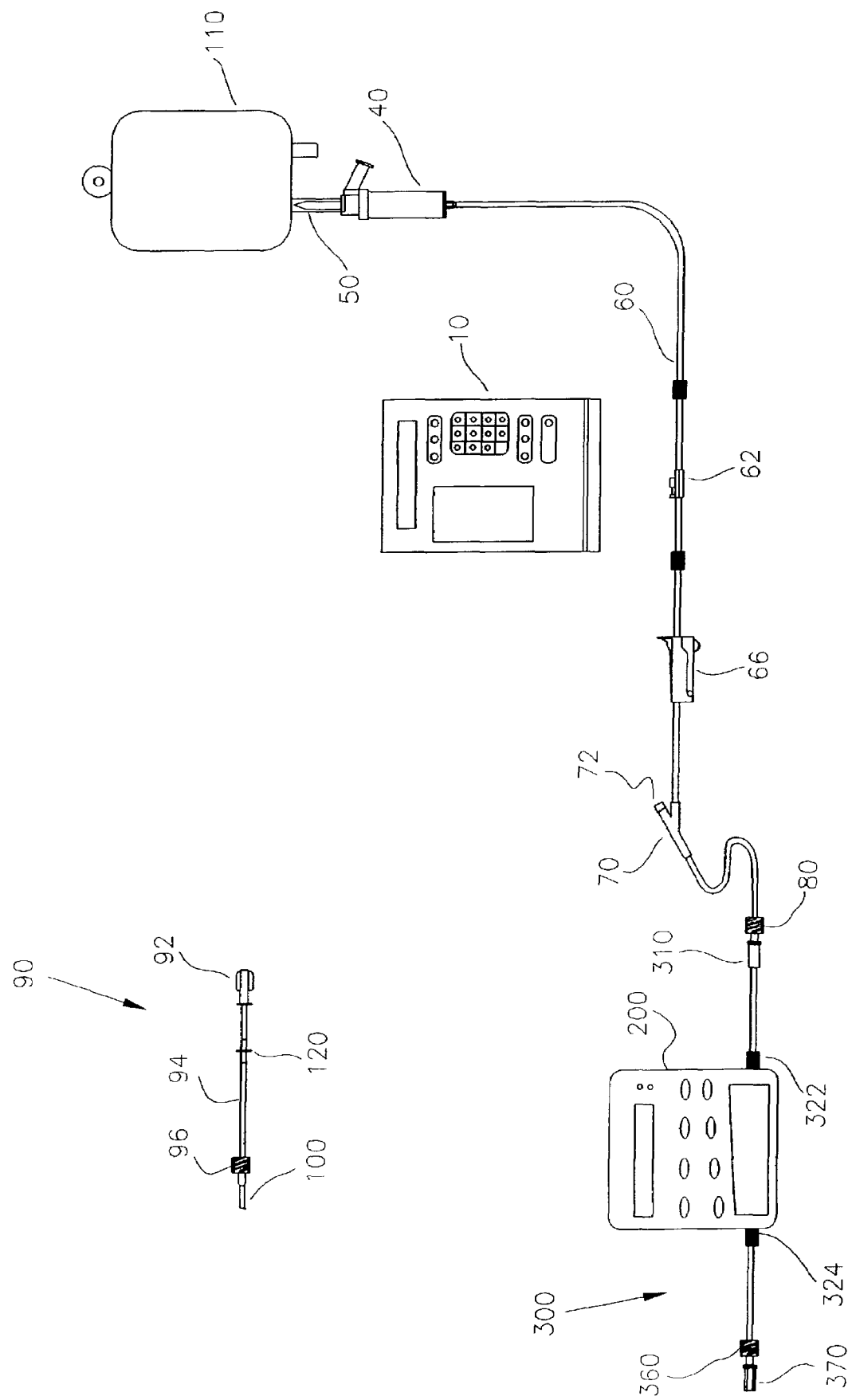
FIG. 9 illustrates removal of the original infusion pump from operative connection with the administration tubing.
Figure 10:
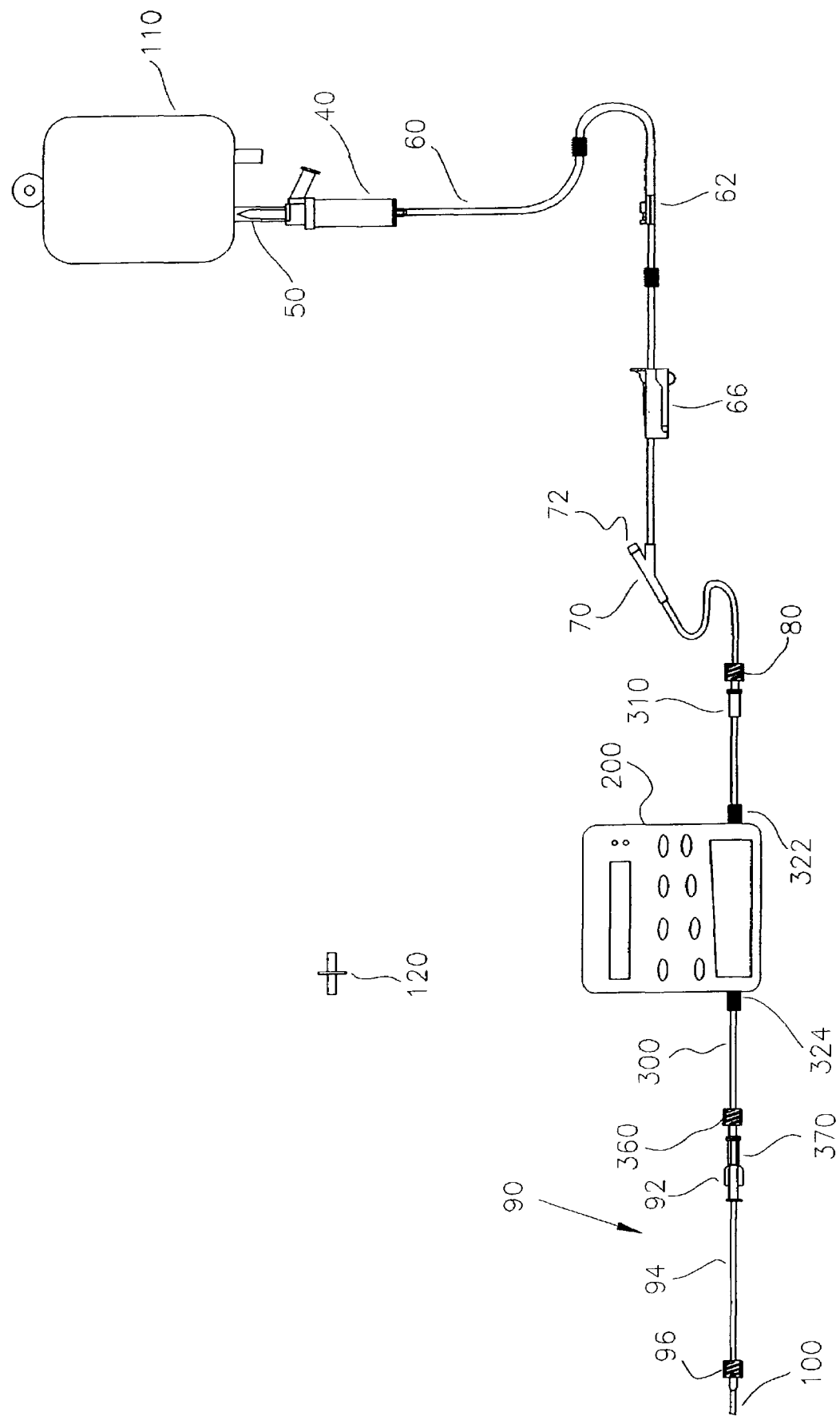
FIG. 10 illustrates connection of the tubing set of the present invention to the patient tubing.

As illustrated in FIG. 8, MR infusion pump 200 is then preferably placed in operative connection with tubing set 300 as known in the art. At this point, infusion pump 10 can be disconnected and removed from tubing set 30 as illustrated in FIG. 9. If priming of the fluid path has not been accomplished with infusion pump 10, infusion pump 200 can now be used to prime the fluid path. Extension set 90 can now be connected to tubing set 300 via valve 370 and luer connector 92 as illustrated in FIG. 10. At this point, infusion pump 200 is in operative connection between IV bag 110 and catheter 100.

Figure 11:
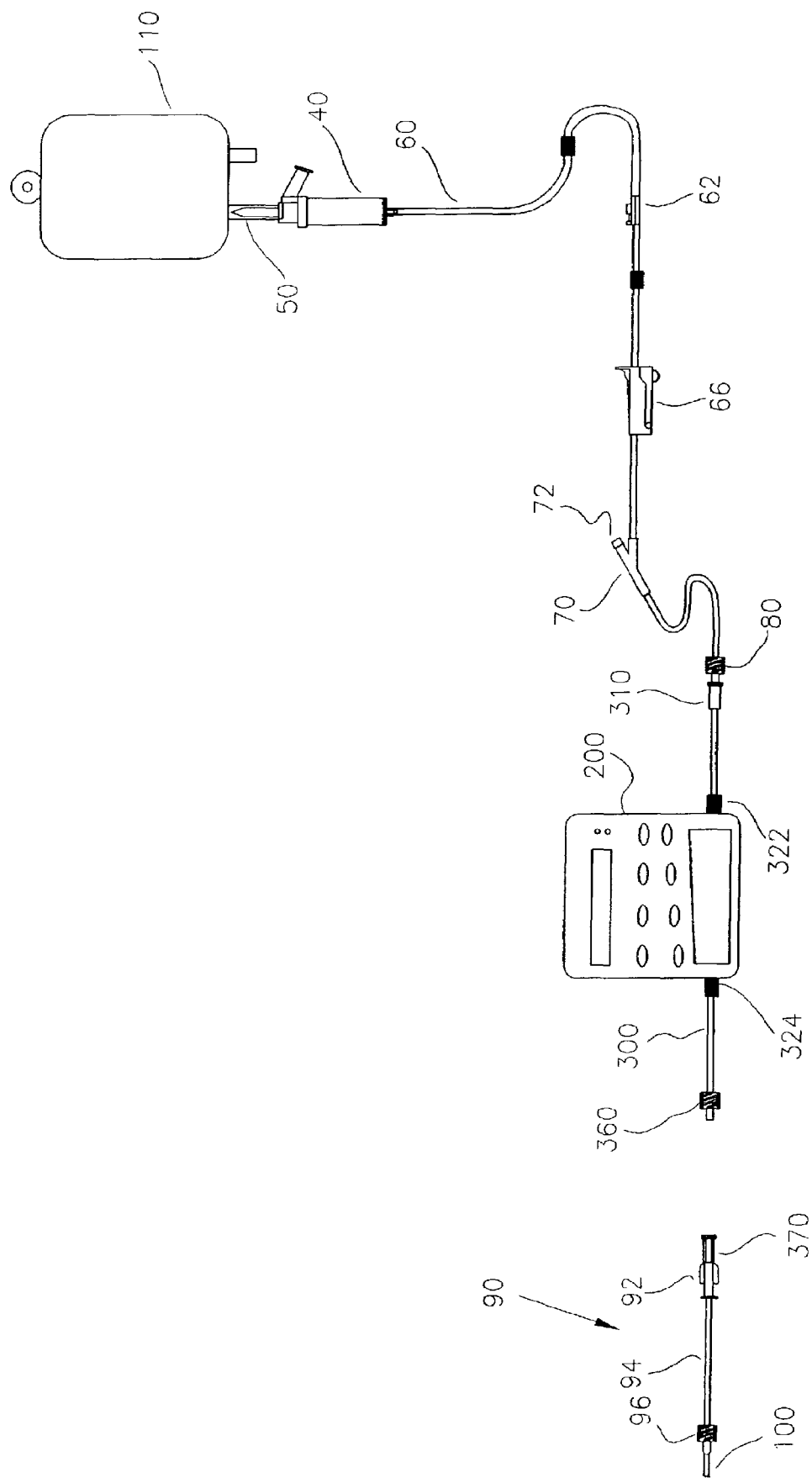
FIG. 11 illustrates disconnection of the tubing set of the present invention from the patient tubing after an injection using the replacement infusion pump.
Figure 12:
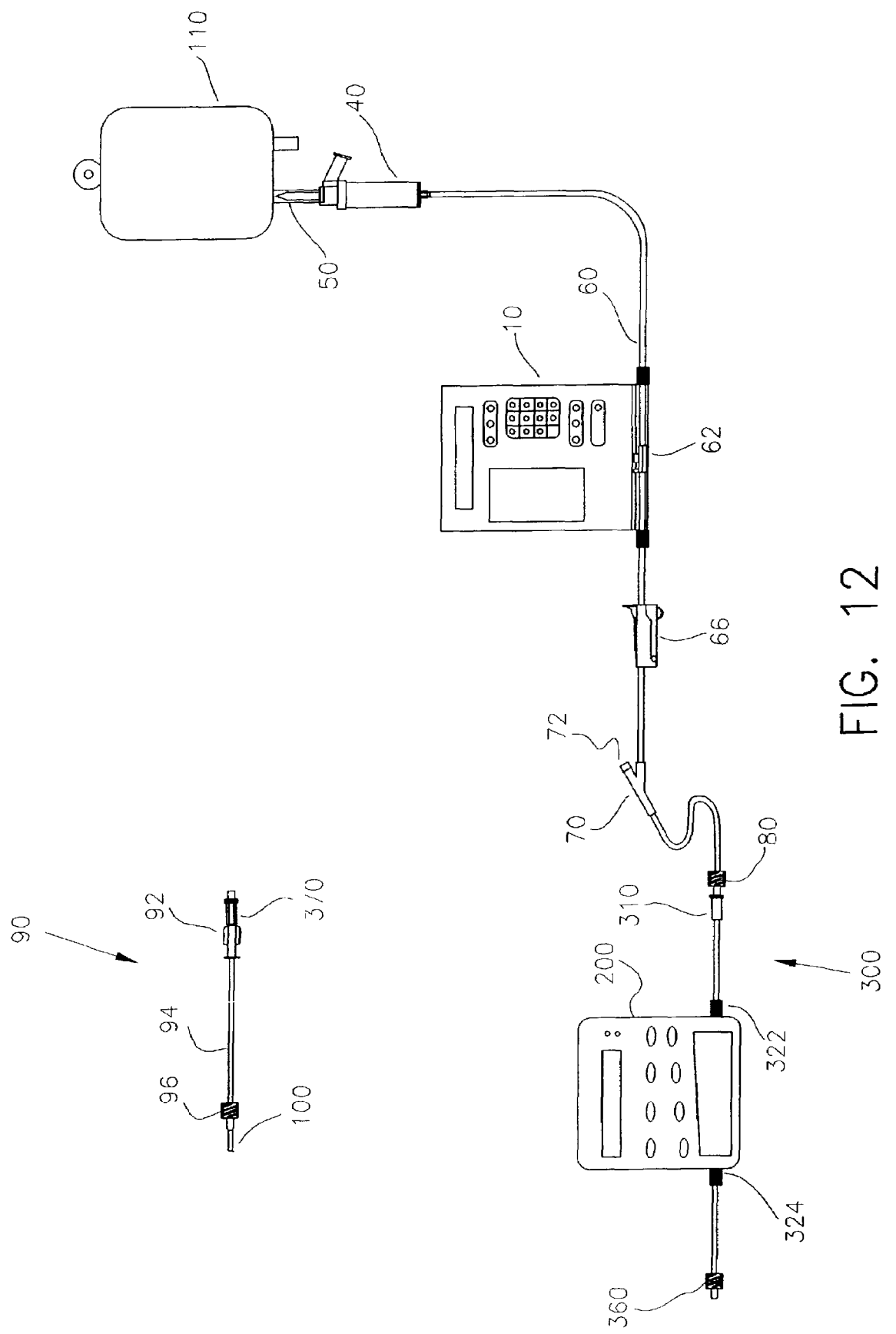
FIG. 12 illustrates reconnection of the original pump to the administration pump.
Figure 13:
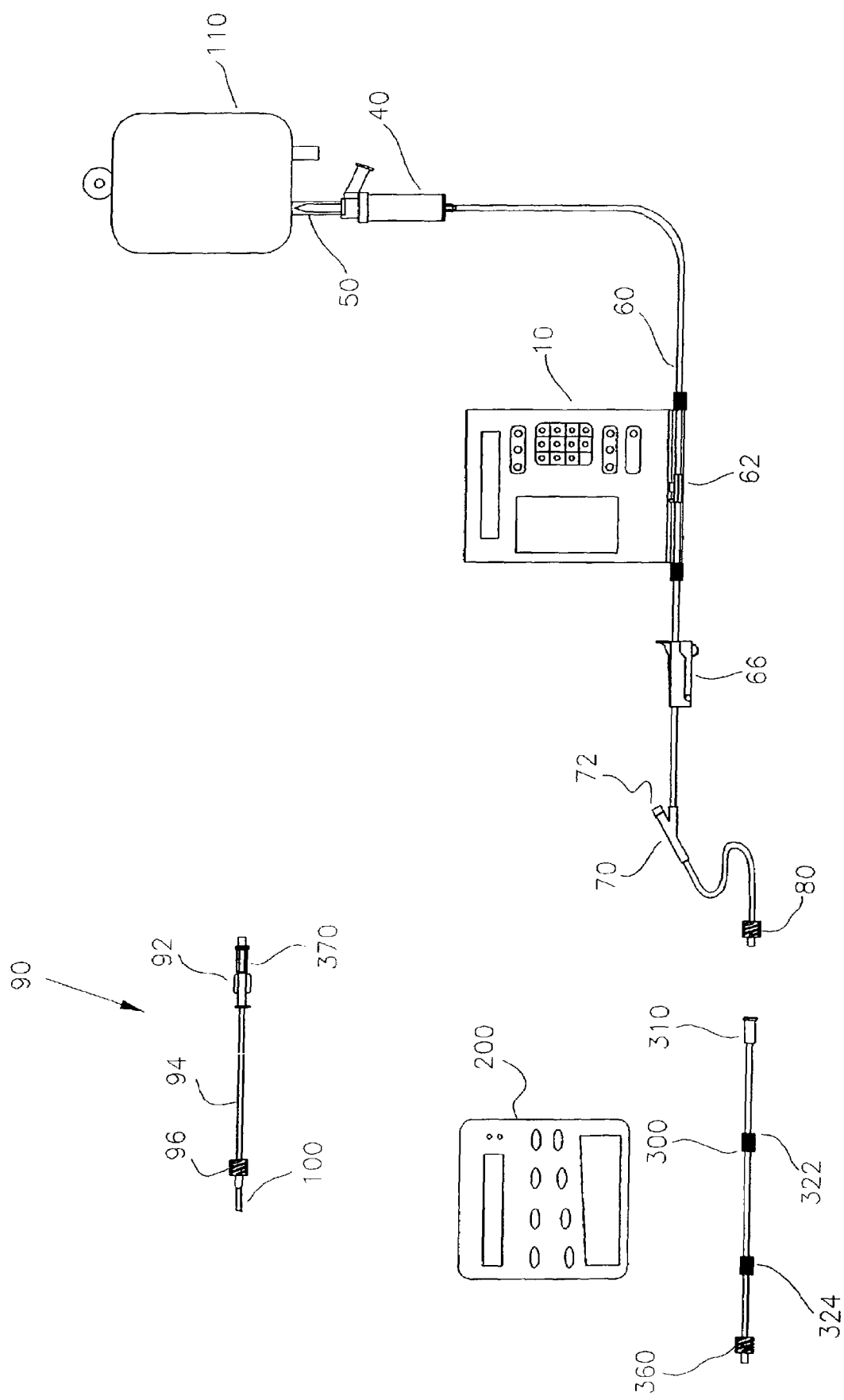
FIG. 13 illustrates disconnection of the replacement pump from the tubing set of the present invention and disconnection of that tubing set from the administration tubing.
Figure 14:
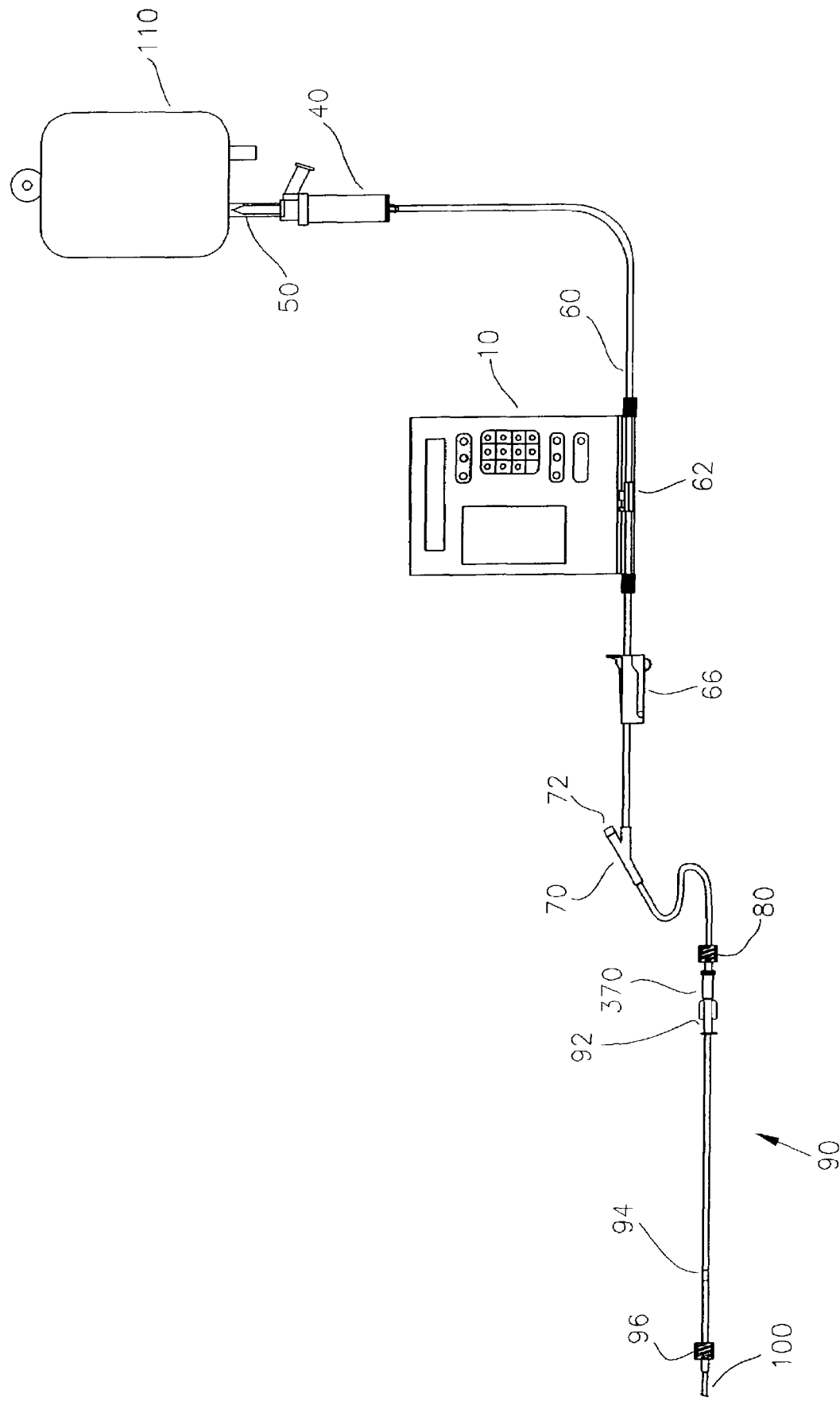
FIG. 14 illustrates reconnection of the patient tubing to the administration tubing.

Once infusion in the MR environment is complete or at some later time, extension set 90 can be disconnected from tubing set 300 by disconnecting male luer 350 from valve 370. As illustrated in FIG. 11, valve 370 (or other flow stop component) is preferably maintained in connection with extension set 90 to prevent backflow of blood and to enable subsequent airless, aseptic reconnection to tubing set 30. A clamp such as clamp 120 can also, for example, be reinstalled on extension set 90 to prevent backflow of blood. As illustrated in FIG. 12, infusion pump 10 can now be reconnected to tubing set 30. Infusion pump 200 can be disconnected from tubing set 300 and tubing set 300 disconnected from luer connector 80 as illustrated in FIG. 13. At this point, an operator can wipe the valve member of valve 370 with, for example, a material carrying a disinfectant (for example, a cotton ball) to easily clean/disinfect the entire surface of the valve member. As illustrated in FIG. 14, tubing set 60 can now be reconnected to extension set 90 by connection of luer connector 80 and valve member 370. At this point, infusion pump 10 is ready to pump fluid from IV bag 110.

In many cases it may be desirable to remove MR infusion pump 200 from the fluid path immediately after the MR procedure is completed. For example, MR infusion pump 200 may be of limited functionality compared to infusion pump 10, there may be a limited supply of MR infusion pumps 200 at a facility, or operator familiarity with the operation of MR infusion pump 200 may be limited as compared to operator familiarity with the operation of infusion pump 10.

In removing tubing set 300 from the fluid path as described above, some injection fluid is going to be removed from the fluid path (that is, an amount generally equal to the volume of tubing 300). It may be desirable, to account for such lost fluid volume in the future programmed delivery of the injection fluid to the patient. In general, it may be desirable to provide for communication/accumulation of information regarding, for example, the amount of fluid delivered by pump 10 and the amount of fluid delivered by pump 200. This can be accomplished, for example, by direct communication between pump 10 and pump 200 (via, for example, an Ethernet network or direct cable connection) or through operator assisted communication. For example, an operator can write the volume injected, flow rate etc. for MR infusion pump 200 during its operation and transfer that information to pump 10 when it is reconnected to the fluid path. Information can also be transferred from infusion pump 10 to infusion pump 200. Paper labels on the pumps, a chart positioned on the IV pole or a patient chart can, for example, be used to record and transfer the information.

The present invention provides for simple and efficient replacement or substitution of an infusion pump or pumps with another infusion pump or pumps without, for example, discarding the tubing set provided with the initial pump(s). In the case of tubing sets having a Y-connector (for example, Y-connector port 72) or other port to which fluid path elements can be connected (via, for example, luer connections), a tubing set of the present invention such as tubing set 300a can be attached to the Y-connector via, for example, aseptic luer connector 370a. Spike 400a can be used to, for example, respike IV bag 110. Infusion pump 10 can be removed from tubing set 60 and MR infusion pump 200 connected to tubing set 300a. Roll clamp 66 can be used to prevent backflow through tubing 60.

Figure 15A:
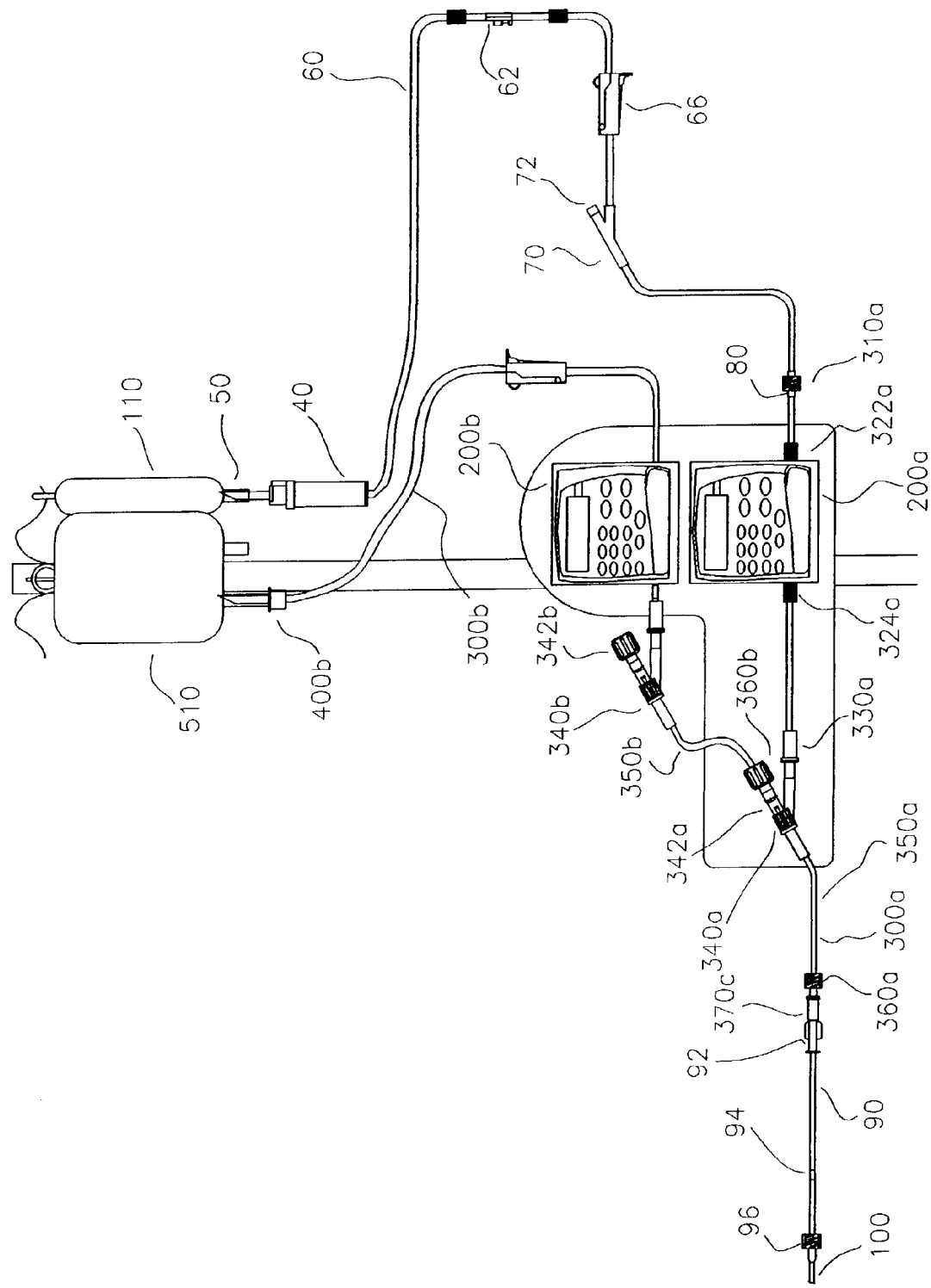
FIG. 15A illustrates a dual pump system of the present invention.
Figure 15B:
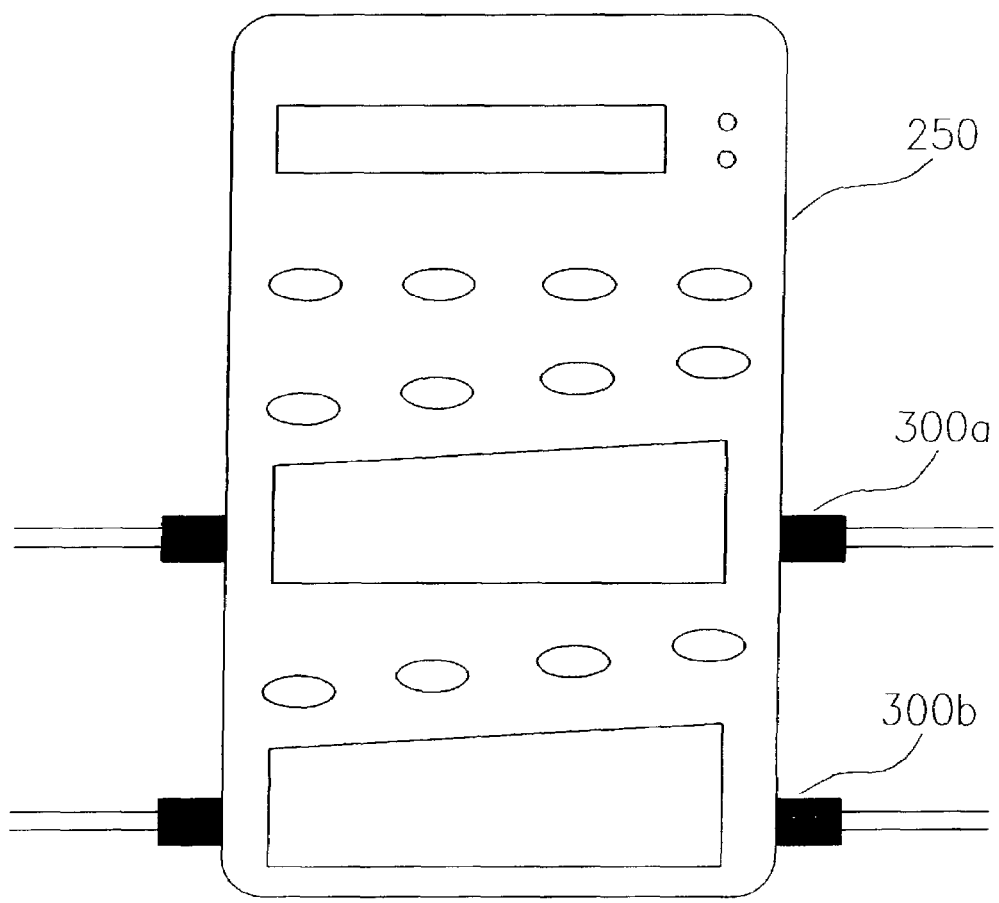
FIG. 15B illustrates a multi-channel infusion pump of the present invention.

As illustrated in FIG. 15A, a plurality of MR infusion pumps 200a and 200b (as described above in connection with infusion pump 200) can be used in the present invention. For example, two infusion pumps 10 may be connected to a patient that are to be replaced by infusion pumps 200a and 200b. Alternatively a multi-path or multi-channel infusion pump with two lines passing therethrough may be connected to a patient and be replaced with infusion pumps 200a and 200b. In general, MR infusion pump 200a is connected to tubing set 300a and extension set 90 generally as described above in connection with infusion pump 200 and tubing set 30. Another tubing set 300b is connected to female luer connector 342a of Y-connector 340a. Second infusion pump 200b is placed in operative connection with tubing set 300b. A spike 400b connected to tubing set 300b is connected to an IV bag 510. Tubing set 300b preferably includes a Y-connector 340b having a female luer connector 342b on one port thereof as described above in connection with tubing set 300a. One port of Y connector 340b is connected to a length of tubing 350b, which is connected female luer connector 342a via a standard male luer connector 360b. In FIG. 15B a multi-path MR infusion pump 250 is illustrated that can be used to replace two infusion pumps 10 or another multi-path infusion pump.

Figure 16:
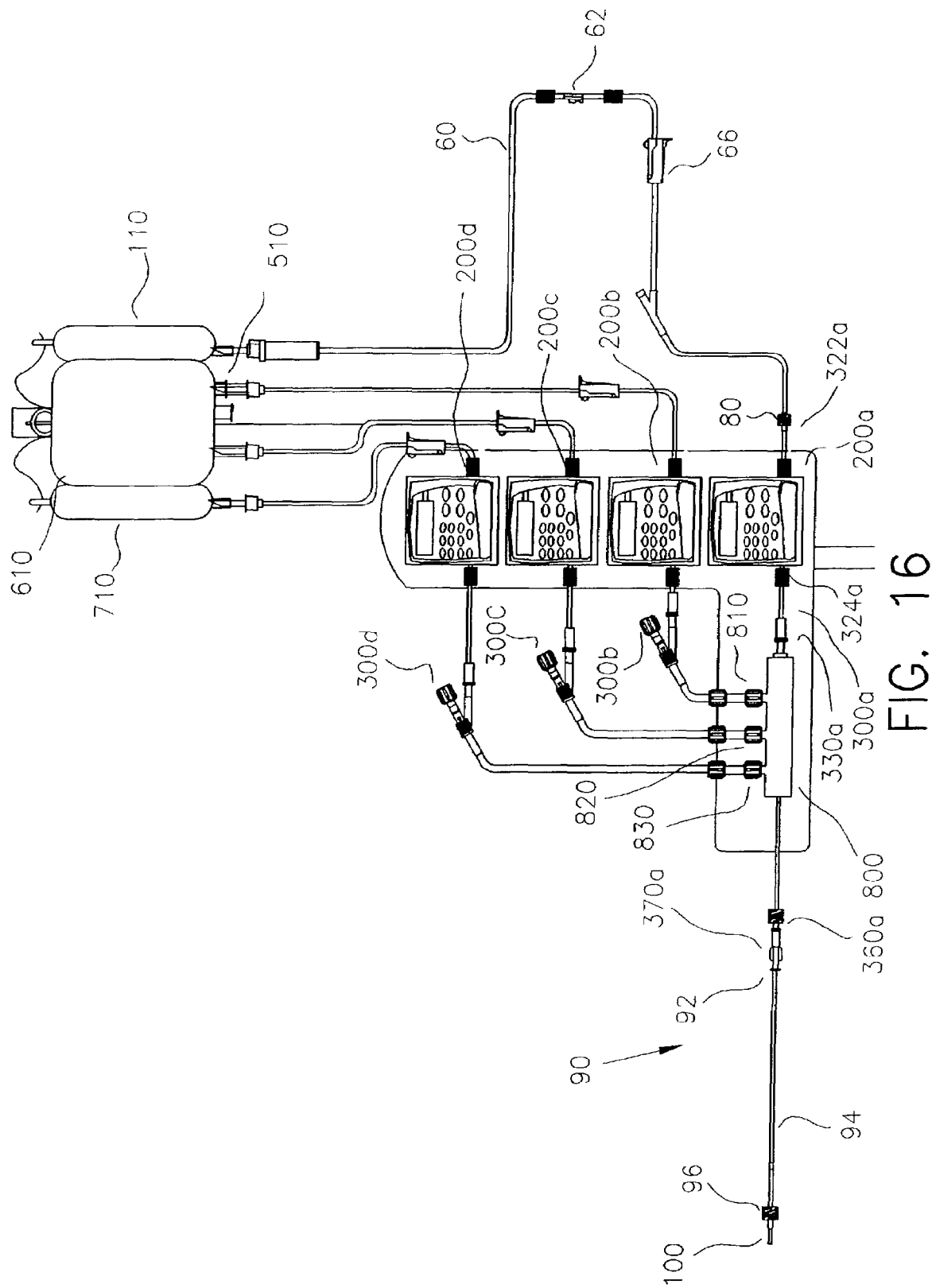
FIG. 16 illustrates a system of the present invention including four infusion pumps connected to four tubing sets.

Many configurations with multiple MR infusion pumps as described above are possible. For example, FIG. 16 illustrates one embodiment in which four MR infusion pumps 200*a*, 200*b*, 200*c* and 200*d* are each connected to separate IV bags 110, 510, 610 and 710, respectively. In the embodiment of FIG. 16, tubing set 3 00*a* includes a three-port fixture 800 in fluid connection therewith between marker 324*a* and valve 370. Each of tubing sets 300*b*, 300*c* and 300*d* is connected to a port 810, 820 and 830, respectively, (for example, via standard luer connectors) of three-port fixture 800. In the embodiment of FIG. 16, tubing sets 300*c* and 300*d* are similar in configuration to tubing set 300*b* as described above. The system of FIG. 16 can, for example, be used to replace four infusion pumps 10 or a single, four-channel infusion pump.

Although the present invention has been described in detail in connection with the above examples, it is to be understood that such detail is solely for that purpose and that variations can be made by those skilled in the art without departing from the spirit of the invention. The scope of the invention is indicated by the following claims rather than by the foregoing description. All changes to the present invention that fall within the meaning and range of equivalency of the claims are to be embraced within their scope.

What is claimed is:

1. A method of temporarily substituting a first microprocessor controlled infusion pump for delivering fluid to a patient with a second microprocessor controlled infusion pump, the first microprocessor controlled infusion pump being incompatible for use within a magnetic resonance imaging (MRI) environment and being for operating upon an administration tubing set for the purpose of pumping the fluid therethrough according to programming thereof, the administration tubing set being in fluid communication with a source of injection fluid and the patient, the method comprising the steps of:
    (a) providing the second microprocessor controlled infusion pump to be temporarily substituted for the first microprocessor controlled infusion pump, the second microprocessor controlled infusion pump being compatible for use within the MRI environment;
    (b) providing a second tubing set having at least one portion thereof that is operable to function with the second microprocessor controlled infusion pump;
    (c) connecting the second tubing set to the administration tubing set to establish an altered fluid path from the source of injection fluid to the patient, the altered fluid path including at least portions of both the administration tubing set and the second tubing set;
    (d) placing the second microprocessor controlled infusion pump for operation upon the at least one portion of the second tubing set for the purpose of enabling the second microprocessor controlled infusion pump to pump the injection fluid therethrough according to programming thereof; and
    (e) disconnecting the first microprocessor controlled infusion pump from the administration tubing set before bringing the patient into the MRI environment wherein the patient may be subjected to at least one of imaging and spectroscopy procedures.

2. The method of claim 1 further comprising the step of priming the altered fluid path using at least one of the first microprocessor controlled infusion pump and the second microprocessor controlled infusion pump.

3. The method of claim 1 further comprising the step of, after disconnecting the first microprocessor controlled infusion pump from the administration tubing set, pumping the injection fluid through the altered fluid path and into the patient using the second microprocessor controlled infusion pump according to the programming thereof.

4. The method of claim 1 wherein the step of connecting the second tubing set to the administration tubing set to establish the altered fluid path includes connecting the second tubing set in series with the administration tubing set.

5. A method of temporarily substituting a first microprocessor controlled infusion pump for delivering fluid to a patient with a second microprocessor controlled infusion pump, the first microprocessor controlled infusion pump being incompatible for use within a magnetic resonance imaging (MRI) environment and being for operating upon an administration tubing set for the purpose of pumping the fluid therethrough according to programming thereof, the administration tubing set being in fluid communication with a source of injection fluid and the patient, the method comprising the steps of:
    (a) providing the second microprocessor controlled infusion pump to be temporarily substituted for the first microprocessor controlled infusion pump, the second microprocessor controlled infusion pump being compatible for use within the MRI environment;
    (b) providing a second tubing set having at least one portion thereof that is operable to function with the second microprocessor controlled infusion pump;
    (c) after permitting the first microprocessor controlled infusion pump to operate upon the administration tubing set and thus pump the fluid therethrough and into the patient, stopping the first microprocessor controlled infusion pump from operating upon the administration tubing set and thus stopping the flow of the fluid into the patient;
    (d) connecting the second tubing set to the administration tubing set to establish an altered fluid path from the source of injection fluid to the patient, the altered fluid path including at least portions of both the administration tubing set and the second tubing set;
    (e) placing the second microprocessor controlled infusion pump upon the at least one portion of the second tubing set for the purpose of enabling the second microprocessor controlled infusion pump to operate thereon and thus pump the injection fluid therethrough;
    (f) disconnecting the first microprocessor controlled infusion pump from the administration tubing set before bringing the patient into the MRI environment wherein the patient may be subjected to at least one of imaging and spectroscopy procedures;
    (g) after disconnecting the first microprocessor controlled infusion pump from the administration tubing set, activating the second microprocessor controlled infusion pump so that according to programming thereof the second microprocessor controlled infusion pump operates upon the second tubing set so as to cause the pumping of the injection fluid through the altered fluid path and into the patient; and
    (h) while the patient is in the MRI environment, continuing as necessary use of the second microprocessor controlled infusion pump to pump the fluid into the patient.

6. The method of claim 5 wherein the step of stopping the first microprocessor controlled infusion pump from operating upon the administration tubing set and thus stopping the flow of the fluid into the patient may also include the use of a clamp being placed upon the administration tubing set.

7. The method of claim 5 further comprising the additional step of, after performance of steps (d) and (e) but before performance of before steps (f) and (g), priming the altered fluid path using at least one of the first microprocessor controlled infusion pump and the second microprocessor controlled infusion.

8. The method of claim 5 further comprising the additional step of, after performance of steps (d), (e) and (f) but before performance of before step (g), priming the altered fluid path using the second microprocessor controlled infusion.

* * * * *